(12) United States Patent
Gilbride et al.

(10) Patent No.: US 12,121,455 B2
(45) Date of Patent: Oct. 22, 2024

(54) INTERVERTEBRAL IMPLANT AND METHOD OF USE

(71) Applicant: Elevation Spine, Inc., Salinas, CA (US)

(72) Inventors: Charles Gilbride, Salinas, CA (US); Trevor Lewis, Lehi, UT (US); Andrew Fauth, North Logan, UT (US)

(73) Assignee: Elevation Spine, Inc., Salinas, CA (US)

( * ) Notice: Subject to any disclaimer, the term of this patent is extended or adjusted under 35 U.S.C. 154(b) by 32 days.

(21) Appl. No.: 18/053,632

(22) Filed: Nov. 8, 2022

(65) Prior Publication Data

US 2023/0083040 A1  Mar. 16, 2023

Related U.S. Application Data

(63) Continuation of application No. 16/344,676, filed as application No. PCT/US2017/058364 on Oct. 25, 2017, now Pat. No. 11,491,025.

(60) Provisional application No. 62/412,732, filed on Oct. 25, 2016.

(51) Int. Cl.
*A61F 2/44* (2006.01)
*A61F 2/30* (2006.01)
*A61F 2/28* (2006.01)

(52) U.S. Cl.
CPC .......... *A61F 2/447* (2013.01); *A61F 2/30749* (2013.01); *A61F 2/442* (2013.01); *A61F 2002/2835* (2013.01); *A61F 2002/30131* (2013.01); *A61F 2002/30176* (2013.01); *A61F 2002/30179* (2013.01); *A61F 2002/30289* (2013.01); *A61F 2002/30426* (2013.01); *A61F 2002/30433* (2013.01); *A61F 2002/30481* (2013.01); *A61F 2002/30879* (2013.01)

(58) Field of Classification Search
CPC ...... A61F 2/4455; A61F 2/446; A61F 2/4465; A61F 2/447; A61F 2/30749
See application file for complete search history.

(56) References Cited

U.S. PATENT DOCUMENTS

| | | | |
|---|---|---|---|
| 6,447,546 B1 * | 9/2002 | Bramlet | A61F 2/446 623/17.11 |
| 2014/0114415 A1 * | 4/2014 | Tyber | A61F 2/4455 623/17.16 |
| 2016/0220384 A1 * | 8/2016 | Donner | A61F 2/4455 |
| 2017/0246007 A1 * | 8/2017 | Chataigner | A61F 2/4425 |

* cited by examiner

*Primary Examiner* — Si Ming Ku
(74) *Attorney, Agent, or Firm* — David Meibos; Maywood IP Law

(57) ABSTRACT

An implant and method for fusing adjacent spinal vertebrae is disclosed. In an embodiment for a spinal implant of the present invention, the implant includes a spacer body assembly and two retention members. The two retention members each include split fork tangs wherein the tangs of each retention member are simultaneously extendable from the spacer body assembly into the adjacent vertebra. A method of fusing adjacent vertebrae includes the step of inserting an implant between adjacent vertebrae with retention members. The method also includes the step of configuring the retention members wherein a portion of each tang of a retention member simultaneously extends from the implant into one of the adjacent vertebra.

21 Claims, 11 Drawing Sheets

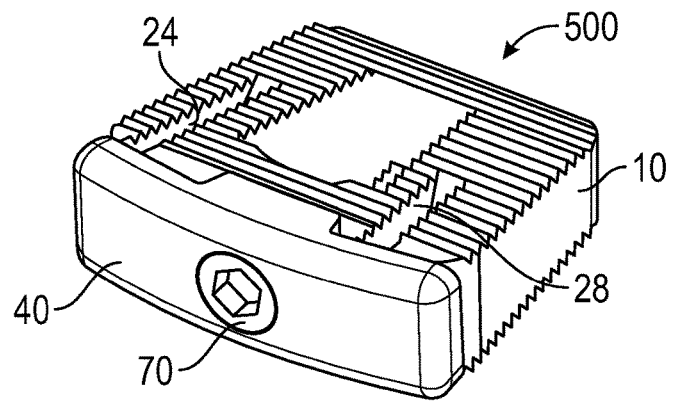
FIG. 22B
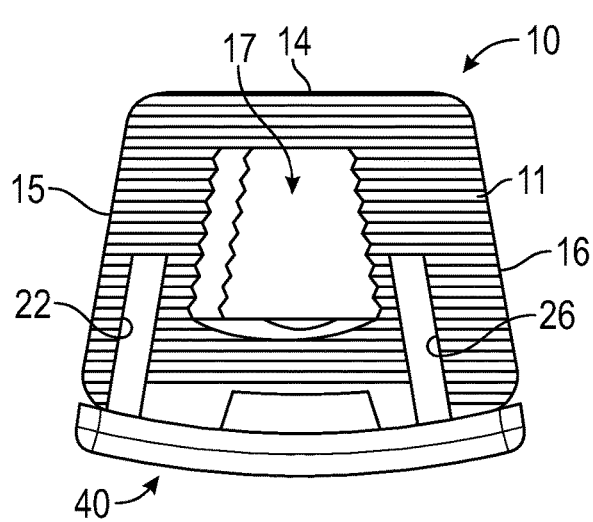 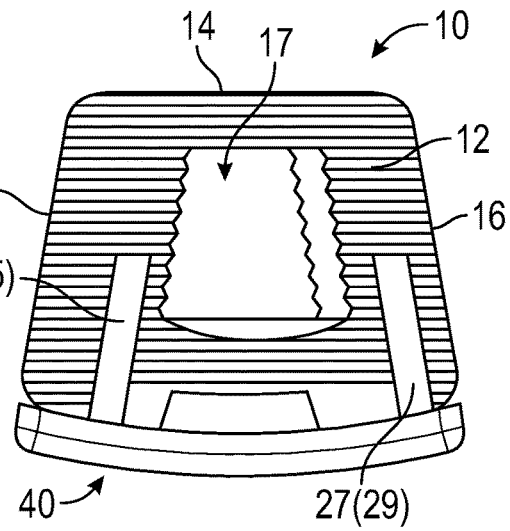
FIG. 22C  FIG. 22D
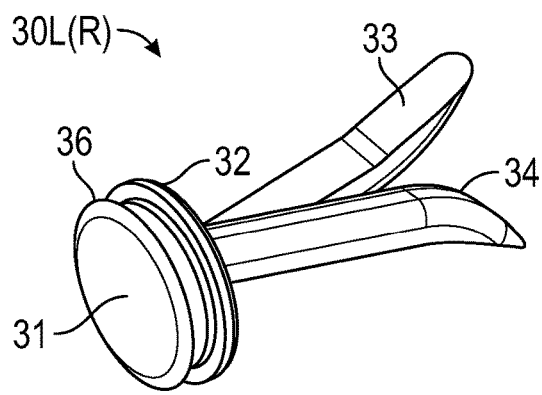 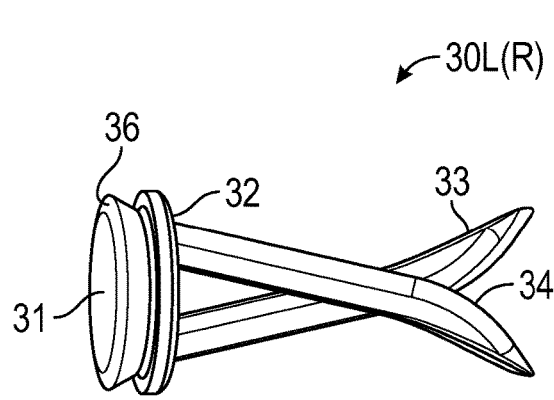
FIG. 23A  FIG. 23B

INTERVERTEBRAL IMPLANT AND METHOD OF USE

CROSS-REFERENCE TO RELATED APPLICATIONS

This application is a continuation of U.S. patent application Ser. No. 16/344,676 filed on Apr. 24, 2019, entitled "Intervertebral Implant and Method of Use", which issued on Nov. 8, 2022, as U.S. Pat. No. 11,491,025, which is a U.S. national stage filing under 35 U.S.C. § 371 of International Application No. PCT/US2017/058364, filed on Oct. 25, 2017, which claims the benefit of U.S. Provisional Application No. 62/412,732, filed on Oct. 25, 2016. All of the foregoing are incorporated as though set forth herein in their entirety.

BACKGROUND OF THE INVENTION

The present disclosure relates generally to orthopedics, and in particular relates to fixation systems, intervertebral implants, and associated surgical methods and procedures for using same.

SUMMARY OF THE INVENTION

Spinal fixation systems such as pedicle screw and rod constructs are commonly used to promote fusion between intervertebral bodies. The insertion of pedicle screws typically requires a linear "line-of-approach" trajectory that is aligned with the longitudinal axis of the screw, in order to accommodate the access and delivery instruments. Similarly, anchors such as bone screws may be used to directly fix intervertebral implants to vertebral bodies, typically requiring the insertion of several screws at unique angles oblique to the sagittal and/or transverse plane, and thus multiple lines-of-approach. However, in a variety of surgical situations, achieving a desired trajectory for screw insertion can be difficult due to the patient's anatomy obstructing a linear line-of-approach. What is therefore desirable are spinal fixation systems that allow for the creation of rigid constructs when the linear line-of-approach for insertion of fixation anchors is unavailable and/or undesirable (e.g., when multiple anchors are required), while at the same time providing increased rigidity and robustness to spinal constructs such as those used in unilateral fusion procedures.

Provided herein is an intervertebral implant for positioning between a first vertebra and a second vertebra successive to the first vertebra, the intervertebral implant comprising a singular spacer body comprising: a superior surface configured to contact an inferior endplate of the first vertebra, an inferior surface configured to contact a superior endplate of the second vertebra, an anterior wall, a posterior wall, a first lateral wall extending between the posterior wall and the anterior wall, a second lateral wall extending between the posterior wall and the anterior wall, and an interior graft window defined by the anterior wall, the posterior wall, the first lateral wall and the second lateral wall, the interior graft window comprising; a graft aperture open to either the superior surface, the inferior surface or both the superior surface and the inferior surface, a first split-guide in the anterior wall, the first split-guide comprising: a first ramped channel extending from the anterior surface to the superior surface within the first lateral wall; and a second ramped channel extending from the anterior surface to the inferior surface within the same first lateral wall.

In some embodiments, the intervertebral implant further comprises a first bone fixation member, also called a retainer, comprises: a cap with an anterior and posterior surface; a capture feature on the cap; a first retention tang and a second retention tang forming a split-fork configuration; wherein the first retention tang and second retention tang protrude from the posterior face of the cap.

In some embodiments, the first bone fixation member/retainer is configured to be inserted through the first split-guide wherein the first ramped channel is configured to guide the first retention tang toward the first opening in the anterior surface and the second ramped channel is configured to guide the second retention tang toward the second opening in the inferior surface.

In some embodiments, the intervertebral implant further comprises a first fixation aperture in the anterior wall extending to the interior graft window; an insert plate configured to be coupled to the spacer body within the interior graft window, the insert plate comprising a second fixation aperture extending therethrough configured to coaxially align with the first fixation aperture; wherein the first fixation aperture and second fixation aperture are configured to receive a locking mechanism.

In some embodiments, the intervertebral implant further comprises a second split-guide in the anterior wall, the second split-guide comprising: a third ramped channel extending from the anterior surface to the superior surface within the second lateral wall; and a fourth ramped channel extending from the anterior surface to the inferior surface within the same second lateral wall.

In some embodiments, the intervertebral implant further comprises a second bone fixation member/retainer comprising: a cap with an anterior and a posterior surface; a capture feature on the cap; a third retention tang and fourth retention tang forming a split fork configuration; wherein the third retention tang and fourth retention tang protrude from the posterior face of the cap.

In some embodiments, the second bone fixation member/retainer is configured to be inserted through the second split-guide wherein the third ramped channel is configured to guide the third retention tang toward the third opening in the anterior surface and the fourth ramped channel is configured to guide the fourth retention tang toward the fourth opening in the inferior surface.

In some embodiments, the first or second split-guide is configured to receive the first or second bone fixation member/retainer comprising a cap with two retention tangs and provide a guided pathway to simultaneously direct the two retention tangs in opposite directions such that when the bone fixation member/retainer is impacted, the first of two tangs at least partially penetrates the inferior endplate of the adjacent superior vertebra and the second of two tangs simultaneously, at least partially penetrates the superior endplate of the adjacent inferior vertebra.

In some embodiments, the bone fixation member/retainer each comprising two retention tangs, each retention tang having a first end, a lengthwise body and a second end opposite the first end and having the split-fork configuration relative to each other are configured such that the tangs protrude from the cap, wherein the first end of each retention tang is affixed to and protruding from the posterior surface of the cap, each retention tang in a plane parallel to the other retention tang, and wherein the second end of each retention tang is oriented at a non-perpendicular angle to the posterior surface of the cap and each second end is oriented in divergent directions to the other retention tang.

In some embodiments, each retention tang of the bone fixation member is configured such that the lengthwise body of each retention tang is: straight; arcuate or helical between the first end and the second end.

In some embodiments, the first or second split-guide comprises a first of two ramped channels having a first end at the split-guide opening, a lengthwise pathway and a second end providing an opening to the superior surface within a lateral wall; and a second of two ramped channels having a first end at the split-guide opening, a lengthwise pathway and a second end providing an opening to the inferior surface within the same lateral wall; wherein each ramped channel lengthwise pathway is shaped such that the configuration of the lengthwise pathway is: straight, arcuate or helical between the first end and the second end of each respective ramped channel.

In some embodiments of the intervertebral implant, the orientation of the ramp channels is reversed, creating a right-handed orientation, wherein the first opening in the first ramped channel is in the inferior surface of the first lateral wall, the second ramped opening is in the anterior surface of the of the first lateral wall, the third opening in the third ramped channel is in the inferior surface of the second lateral wall and the fourth ramped opening is in the anterior surface of the of the second lateral wall.

In some embodiments the intervertebral implant comprises both left-hand orientation ramp channels and right-hand orientation ramp channels.

In some embodiments, at least one of the two retention tangs further comprises a plurality of substantially inversely shaped "V" notches along the lengthwise body, anywhere between a middle of the lengthwise body and proximate to the second end, the plurality of notches configured to promote resistance to extraction of the retention tang and the overall bone fixation member from a vertebral bone or the spacer body after insertion.

In some embodiments, a tip on the second end of each retention tang is configured to penetrate: a vertebral endplate, a cancellous bone or a cortical bone of a vertebra.

In some embodiments, the bone fixation member comprising helical retention tangs at least partially penetrates the inferior endplate of the superior adjacent vertebra and simultaneously, at least partially penetrate the superior endplate of the inferior adjacent vertebra in a corkscrew manner such that each tang follows a helical path unique to the helix of each retention tang and wherein the entire bone fixation member rotates as it is deployed through the spacer body.

In some embodiments, the bone fixation member comprises a left-handed orientation, wherein the second end of a left retention tang is oriented superiorly at a non-perpendicular angle to the posterior surface of the cap and the second end of a right retention tang is oriented inferiorly at a non-perpendicular angle to the posterior surface of the cap and each second end of the left and right retention tang is oriented in a divergent direction to the other retention tang.

In some embodiments, the intervertebral implant further comprises both a left-handed orientation bone fixation member and a right-handed orientation bone fixation member when fully assembled.

In some embodiments, the intervertebral implant further comprises a retaining clip configured to capture the bone fixation member within the opening of the first or second split-guide.

In some embodiments, the bone fixation member with helical retention tangs comprises a left-handed orientation, wherein the helix is left-handed. In some embodiments, the bone fixation member with helical retention tangs comprises a right handed orientation, wherein the helix is right-handed.

In some embodiments, the bone fixation member comprises a right handed orientation, wherein the helix is right-handed, such that the second end of a right retention tang is oriented superiorly at a non-perpendicular angle to the posterior surface of the cap and the second end of a left retention tang is oriented inferiorly at a non-perpendicular angle to the posterior surface of the cap and each second end of the right and left retention tang is oriented in a divergent helical direction to the other retention tang.

In some embodiments of the intervertebral implant the orientation of the ramp channel is helical, wherein the first opening in a first ramped helical channel is in the inferior surface of the first lateral wall, the second ramped opening in a second ramped helical channel is in the anterior surface of the of the first lateral wall, the third opening in the third ramped helical channel is in the inferior surface of the second lateral wall and the fourth ramped opening in the fourth ramped helical channel is in the anterior surface of the of the second lateral wall.

In some embodiments, the intervertebral implant comprises a right handed helical orientation ramped channel, wherein the helix is right-handed. In some embodiments, the intervertebral implant comprises a left handed helical orientation ramped channel, wherein the helix is left-handed. In still other embodiments, the intervertebral implant comprises both a left-handed and a right-handed helical ramp channel.

In some embodiments, the intervertebral implant further comprises a retaining clip configured to capture the bone fixation member within the split-guide aperture.

In some embodiments, the intervertebral implant further comprises a faceplate or spinal cage fixation plate and a locking mechanism; wherein the faceplate or spinal cage fixation plate comprises an anterior face, a stepped posterior face, top edge, a bottom edge spaced apart from the top edge, a first lateral edge and a second lateral edge, wherein the faceplate or spinal cage fixation plate further comprises a third fixation aperture extending therethrough and a counter-bore, both the third fixation aperture and the counter-bore configured to coaxially align with the first and second fixation aperture, wherein the locking mechanism is configured to pass through the third fixation aperture and into the first and second fixation apertures to securely retain the faceplate or spinal cage fixation plate against the anterior wall of the spacer body, and wherein a locking mechanism head or cap is captured within the counter-bore.

In some embodiments, the faceplate or spinal cage fixation plate is further configured to be a secondary capture mechanism for at least the first bone fixation member to prevent unintentional removal thereof.

In some embodiments, the first and second bone fixation member each comprising two retention tangs, are provided with the spacer body, inserted at least partially into the first and second split-guide aperture, wherein the first, second, third and fourth tangs are in a compressed, non-deployed state.

In some embodiments, the first and second bone fixation member each comprising two retention tangs, are provided with the faceplate in an orientation configured to match that of the channels in the split-guides.

In some embodiments, the first, second, third and fourth tangs become decompressed and at least partially penetrate the adjacent vertebra when the first and second bone fixation members are pushed into the first and second guide openings.

In some embodiments, the locking mechanism comprises: a screw; a bolt; a bayonette connection; a pin; a tapered pin or a split-compression pin.

Provided herein is a method of fusing a first vertebra and a second vertebra successive to the first vertebra, comprising the steps of: inserting a spacer body between prepared facing surfaces of the first vertebra and a second vertebra, the spacer body comprising a superior surface, an inferior surface and an interior graft window defined by an anterior wall, a posterior wall, a first lateral wall, and a second lateral wall; inserting a first retainer in a compressed configuration into a first split-guide aperture extending from the anterior wall into the first lateral wall of the spacer body, the first retainer comprising a first tang and a second tang, said first and second tangs comprising a split-fork configuration relative to one another; driving the first retainer fully into the first split-guide aperture such that the first tang engage a first ramped channel and extends out of a first opening on the superior surface of the first lateral wall and the second tang simultaneously engages a second ramped channel and extends out of a second opening on the inferior surface of the first lateral wall; and wherein the first tang is configured to at least partially penetrate the first adjacent vertebra and simultaneously, the second tang is configured to at least partially penetrate the second adjacent vertebra, creating a decompressed configuration for the first tang and the second tang.

In some embodiments, the method comprises inserting a second retainer in a compressed configuration into a second split-guide aperture extending from the anterior wall into the second lateral wall of the spacer body, the second retainer comprising a third tang and a fourth tang, said third and fourth tangs comprising a split-fork configuration relative to one another; driving the second retainer fully into the second split-guide aperture such that the first tang engages a third ramped channel and extends out of a third opening on the superior surface of the second lateral wall and the fourth tang simultaneously engages a fourth ramped channel and extends out of a fourth opening on the inferior surface of the second lateral wall; and wherein the third tang is configured to at least partially penetrate the first adjacent vertebra and simultaneously, the second tang is configured to at least partially penetrate the second adjacent vertebra, creating a decompressed configuration for the third tang and the fourth tang.

In some embodiments, the method optionally comprises the step of inserting a bone graft material into the graft window prior to inserting the spacer body between the prepared surfaces of the first and second adjacent vertebra.

In some embodiments, the method further comprises the steps of: optionally affixing a faceplate to an anterior surface of the spacer body and securing said faceplate with a locking mechanism; wherein the faceplate is configured to be a secondary capture mechanism for the first and second retention members.

Provided herein is an intervertebral implant kit comprising: a spacer body comprising; a superior surface, an inferior surface, and an interior graft window defined by an anterior wall, a posterior wall, a first lateral wall, and a second lateral wall; and a first split-guide aperture comprising: a first ramped channel extending from the anterior wall into the first lateral wall and to a first opening in the superior surface of the first lateral wall; a second ramped channel extending from the anterior wall into the first lateral wall and to a first opening in the inferior surface of the same first lateral wall; and a first recess at the anterior wall; and a first capture ring configured to be placed in the first recess; wherein the superior surface is configured to contact an inferior endplate of a first adjacent vertebra and the inferior surface is configured to contact a superior endplate of a second adjacent vertebra, a first bone retainer comprising: a first cap with an anterior and posterior surface; a first tang; and a second tang forming a split-fork configuration with the first tang; wherein the first tang and second tang both extend from the posterior surface of the first cap, wherein the first tang and second tang initially both extend from the first cap in a plane generally parallel to each other and end at a first terminus and a second terminus, respectively, and wherein the first terminus of the first tang is oriented at a non-perpendicular angle to the posterior surface of the first cap and the second terminus of the second tang is oriented at a non-perpendicular angle to the posterior surface of the first cap and is oriented in a divergent direction relative to the first terminus of the first tang, wherein the first tang and second tang of the first retainer comprise a compressed configuration prior to delivery into the first split-guide aperture, and wherein upon delivery into the first split-guide aperture, the first and second tangs expand relative to one another and are configured to at least partially penetrate the first adjacent vertebra and the second adjacent vertebra, respectively.

In some embodiments, the kit further comprises a second capture ring, a second retainer comprising: a second cap with an anterior and posterior surface; a third tang; and a fourth tang forming a split-fork configuration with the first tang; wherein the third tang and fourth tang initially both extend from the second cap in a plane generally parallel to each other, and end at a third terminus and a fourth terminus, respectively, wherein the third terminus of the third tang is oriented at a non-perpendicular angle to the posterior surface of the second cap and the fourth terminus of the fourth tang is oriented at a non-perpendicular angle to the posterior surface of the second cap and is oriented in a divergent direction relative to the third terminus of the third tang, and wherein the spacer body further comprises a second split-guide aperture comprising: a third ramped channel extending from the anterior wall into the second lateral wall and to a third opening in the superior surface of the second lateral wall; a fourth ramped channel extending from the anterior wall into the second lateral wall and to a fourth opening in to the inferior surface of the second lateral wall; and a second recess in the anterior wall, wherein the third tang and fourth tang of the second retainer comprise a compressed configuration prior to delivery into the second split-guide aperture, and wherein upon delivery into the second split-guide aperture, the third and fourth tangs expand relative to one another and are configured to at least partially penetrate the first adjacent vertebra and the second adjacent vertebra, respectively.

In some embodiments, the first cap and the second cap are contiguous and/or are attached to one another.

In some embodiments, the intervertebral implant kit further optionally comprises a faceplate and a locking mechanism; wherein the faceplate comprises a first fixation aperture extending therethrough and a counter-bore, both configured to coaxially align with a second fixation aperture in the spacer body, wherein the locking mechanism is configured to pass through the first fixation aperture and into the coaxially aligned second fixation apertures to securely retain the faceplate against the anterior wall of the spacer body, wherein a locking mechanism head or cap is captured within the counter-bore, and wherein the faceplate is further configured to be a secondary capture mechanism for the first and second bone fixation members to prevent unintentional removal thereof.

Provided herein is an intervertebral implant comprising: a singular spacer body comprising a superior surface, an inferior surface, an anterior wall, a posterior wall, a first lateral wall, a second lateral wall that extend between the posterior wall and the anterior wall, and an interior graft window within the spacer body; wherein the superior surface is configured to contact an endplate of a first adjacent vertebra and the inferior surface is configured to contact an endplate of a second adjacent vertebra, and wherein the interior graft window comprises at least one graft aperture open to either the superior surface, the inferior surface or both the superior and inferior surface, a first guide aperture on the anterior wall, the first split-guide aperture comprising: a first ramped channel providing a first opening to the superior surface within the first lateral wall; and a second ramped channel providing a second opening to the inferior surface within the same first lateral wall; a first bone fixation member comprising a cap with a first and second retention tang protruding therefrom configured to be inserted through the first guide aperture and at least partially penetrates the first adjacent vertebra and simultaneously, at least partially penetrates the second adjacent vertebra; wherein the bone fixation member comprises a split fork configuration, a second bone fixation member comprising: a cap with an anterior and posterior surface; a third retention tang and a fourth retention tang forming a split-fork configuration; wherein the third retention tang and fourth retention tang protrude from the posterior face of the cap, wherein the second bone fixation member is configured to be inserted through a second split-guide aperture wherein the third ramped channel is configured to guide the third retention tang toward the third opening in the superior surface and the fourth ramped channel is configured to guide the fourth retention tang toward the fourth opening in the inferior surface.

In some embodiments, the intervertebral implant further comprises: a first fixation aperture in the anterior wall; an insert plate configured to be coupled to the spacer body, the insert plate comprising a second fixation aperture extending therethrough configured to coaxially align with the first fixation aperture; wherein the first fixation aperture and second fixation aperture are configured to receive a locking mechanism.

In some embodiments, the intervertebral implant further comprises: a faceplate and the locking mechanism; wherein the faceplate comprises a third fixation aperture extending therethrough and a counter-bore, both configured to coaxially align with a second fixation aperture in the spacer body, wherein the locking mechanism is configured to pass through the third fixation aperture and into the coaxially aligned second fixation apertures to securely retain the faceplate against the anterior wall of the spacer body, wherein a locking mechanism head or cap is captured within the counter-bore, and wherein the faceplate is further configured to be a secondary capture mechanism for the first bone fixation member to prevent unintentional removal thereof.

Provided herein is an intervertebral implant comprising: a bone fixation member comprising: a cap with an anterior and posterior surface; a capture feature on the cap; a first retention tang and a second retention tang each retention tang having a first end, a lengthwise body and a second end opposite the first end and forming a split-fork configuration relative to each other; wherein the first retention tang and second retention tang protrude from the posterior face of the cap, each retention tang in a plane parallel to the other retention tang.

In some embodiments, the first end of each retention tang is affixed to and protruding from the posterior surface of the cap, wherein the second end of each retention tang is oriented at a non-perpendicular angle to the posterior surface of the cap and each second end is oriented in divergent directions to the other retention tang.

In some embodiments, each retention tang of the bone fixation member is configured such that the lengthwise body of each retention tang is straight, arcuate, or helical between the first end and the second end.

Provided herein is a spinal cage fixation plate comprising: an anterior surface; a stepped posterior surface spaced from the anterior surface along a medial-lateral direction; a superior surface; and an inferior surface spaced from the superior surface along a medial-lateral direction; a first fixation aperture extending from the anterior surface through the posterior surface, configured to receive the shank of a fixation mechanism; and a concentric secondary aperture on the anterior surface, coaxially aligned with the first fixation aperture, configured to receive the head of the fixation mechanism, wherein the first fixation aperture and secondary aperture are centrally located in the medial-lateral and superior-inferior dimensions of the fixation plate, wherein an overall medial-lateral dimension of the plate is greater than a superior-inferior dimension of the plate, and wherein the stepped posterior surface comprises a recessed medial stepped portion, a recessed lateral stepped portion and a posteriorly protruding central portion.

In some embodiments, the surfaces of the recessed medial stepped portion, and the recessed lateral stepped portion are defined as a coaxial cylindrical surface, the curvature approximating that of vertebral bodies to be fused, when viewed from a superior or inferior orientation.

In some embodiments, the posteriorly protruding central portion is configured to align with and interface with a mating recessed surface on an anterior face of a spinal fusion cage, and wherein the first fixation aperture and secondary aperture are configured to coaxially align with a mating third aperture in the anterior portion of said spinal fusion cage and jointly accept a fixation mechanism configured to secure the spinal cage fixation plate to the spinal fusion cage, and wherein the surfaces of the recessed medial stepped portion, and the recessed lateral stepped portion of the spinal cage fixation plate are configured to align with a raised anterior medial stepped portion, and a raised anterior lateral stepped portion of the fusion cage.

In some embodiments, the spinal cage fixation plate further comprises: at least one aperture for receiving a bone screw; wherein the at least one aperture is positioned superiorly to the superior surface of the fixation plate and configured to at least temporarily secure the fixation plate to a superior adjacent vertebra.

In some embodiments, the spinal cage fixation plate further comprises at least a second aperture for receiving a bone screw; wherein the at least second aperture is positioned inferiorly to the inferior surface of the fixation plate and configured to at least temporarily secure the fixation plate to an inferior adjacent vertebra.

In some embodiments, the spinal cage fixation plate further comprises at least one fixation spike; wherein the at least one fixation spike is positioned superiorly to the superior surface of the fixation plate and configured to at least temporarily secure the fixation plate to a superior adjacent vertebra.

In some embodiments, the spinal cage fixation plate further comprises at least a second fixation spike; wherein the at least second fixation spike is positioned inferiorly to the inferior surface of the fixation plate and configured to at least temporarily secure the fixation plate to an inferior adjacent vertebra.

In some embodiments, the spinal cage fixation plate further comprises: anteriorly recessed features in the posterior surfaces of the recessed medial stepped portion, and the recessed lateral stepped portion of the spinal cage fixation plate configured to align with and capture the cap of a bone fixation member protruding from the anterior face of a spinal fusion cage; and a capture ring or retaining clip configured to capture the cap of bone fixation member within the anteriorly recessed feature.

In some embodiments, the spinal cage fixation plate comprises at least one of: a biologically inert material; a sufficiently porous surface to facilitate bony ingrowth; and a biologically active surface coating to facilitate bony ingrowth and spinal fusion.

In some embodiments, the surfaces of the recessed medial stepped portion, and the recessed lateral stepped portion of the spinal cage fixation plate are configured to align with an anterior surface of a superior and inferior vertebra, wherein the posteriorly protruding central portion is configured to fit between and separate the inferior surface of the superior vertebra and superior surface of the inferior vertebra.

In some embodiments, the posteriorly protruding central portion is further configured to prevent the expulsion of a spinal fusion cage positioned between the inferior and superior vertebrae.

In some embodiments, the at least first fixation spike and the at least second fixation spike further comprise at least one: a biologically inert material; a sufficiently porous surface to facilitate bony ingrowth; and a biologically active coating to facilitate bony ingrowth.

In some embodiments, the fixation plate is made of a biologically inert material selected from the group consisting of: an allograft; an autograft; titanium; titanium alloys; PEEK (polyaryl, ether, ether ketone) polymer; cobalt-chromium alloys; tantalum; tantalum alloys; niobium; niobium alloys; and stainless steel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

FIG. 1 is an isometric view of one version of the intervertebral implant with left and right bone fixation members.

FIG. 2 is an exploded isometric view of FIG. 1.

FIG. 3 is a variant of FIG. 1 without a faceplate.

FIG. 4A is an ISO view of the spacer body of the intervertebral implant of FIG. 1.

FIG. 4B is a top view of the spacer body of the intervertebral implant of FIG. 1.

FIG. 4C is a bottom view of the spacer body of the intervertebral implant of FIG. 1.

FIG. 5A is an ISO view of a Right bone fixation member of FIG. 1.

FIG. 5B is an anterior view of a Right bone fixation member of FIG. 1 with the fixation tangs in an expanded state.

FIG. 5C is a top view of a Right bone fixation member of FIG. 1 with the fixation tangs in a compressed state.

FIG. 5D is a side view of a Right bone fixation member of FIG. 1 with the fixation tangs in a compressed state.

FIG. 5E is a side view of a Right bone fixation member of FIG. 1 with the fixation tangs in an expanded state.

FIG. 6A is an ISO view of a Left bone fixation member of FIG. 1.

FIG. 6B is an anterior view of a Left bone fixation member of FIG. 1 with the fixation tangs in an expanded state.

FIG. 6C is a top view of a Left bone fixation member of FIG. 1 with the fixation tangs in a compressed state.

FIG. 6D is a side view of a Left bone fixation member of FIG. 1 with the fixation tangs in a compressed state.

FIG. 6E is a side view of a Left bone fixation member of FIG. 1 with the fixation tangs in an expanded state.

FIG. 7A is an ISO view of a non-limiting representative capture mechanism for a bone fixation member.

FIG. 7B is a front view of the capture mechanism of FIG. 7A.

FIG. 7C is a side view of the capture mechanism of FIG. 7A.

FIG. 7D is a cross-section view of the capture mechanism of FIG. 7B.

FIG. 8A is a superior view of the intervertebral implant of FIG. 3 with left and right bone fixation members partially inserted in the left and right split-guide openings.

FIG. 8B is a cross-section view of the right bone fixation member in a compressed state, before full insertion, within the right ramped channel to the superior surface of the intervertebral implant of FIG. 3.

FIG. 8C is another superior view of the intervertebral implant of FIG. 3 with left and right bone fixation members fully inserted in the left and right split-guide openings.

FIG. 8D is a cross-section view of the right bone fixation member in an expanded state and fully inserted within the ramped channel to the superior surface of the intervertebral implant of FIG. 3.

FIG. 9 is an anterior view of the intervertebral implant of FIG. 3 with left and right bone fixation members.

FIG. 10A is an inferior view of the intervertebral implant of FIG. 3 with left and right bone fixation members partially inserted in the left and right split-guide openings.

FIG. 10B is a cross-section view of the right bone fixation member in a compressed state, before full insertion, within the right ramped channel to the superior surface of the intervertebral implant of FIG. 3.

FIG. 10C is another inferior view of the intervertebral implant of FIG. 3 with left and right bone fixation members fully inserted in the left and right split-guide openings.

FIG. 10D is a cross-section view of the right bone fixation member in an expanded state and fully inserted within the ramped channel to the inferior surface of the intervertebral implant of FIG. 3.

FIG. 11 is a side view of the intervertebral implant of FIG. 3 with left and right bone fixation members.

FIG. 12 is an exploded ISO view of another variant of the intervertebral implant of FIG. 3 with a non-limiting representative faceplate/spinal cage fixation plate.

FIG. 13A is a superior view of the faceplate/spinal cage fixation plate of FIG. 12.

FIG. 13B is an anterior view of the faceplate/spinal cage fixation plate of FIG. 12.

FIG. 13C is a side view of the faceplate/spinal cage fixation plate of FIG. 12.

FIG. 14 is a non-limiting representative insert plate with a capture aperture, as shown in FIG. 2

FIG. 15A is an ISO view of a non-limiting representative capture mechanism of FIG. 12.

FIG. 15B is a top view of a non-limiting representative capture mechanism of FIG. 12.

FIG. 16 is an exploded ISO view of another variant of the intervertebral implant of FIG. 3 with a non-limiting representative bone fixation member locking plate.

FIG. 17A is a superior view of the intervertebral implant of FIG. 16 with left and right bone fixation members partially inserted in the left and right split-guide openings.

FIG. 17B is an anterior view of the intervertebral implant of FIG. 16 with left and right bone fixation members.

FIG. 17C is an inferior view of the intervertebral implant of FIG. 16 with left and right bone fixation members partially inserted in the left and right split-guide openings.

FIG. 18A is a detail of the left bone fixation member fully inserted in ramped channel to the superior and with the bone fixation member locking plate engaged.

FIG. 18B is a close-up detail view of the bone fixation member locking plate engaged in the bone fixation member capture groove.

FIG. 19A is an ISO view of a representative non-limiting bone fixation member locking plate.

FIG. 19B is a superior view of the bone fixation member locking plate of FIG. 19A.

FIG. 19C is an anterior view of the bone fixation member locking plate of FIG. 19A.

FIG. 19D is a side view of the bone fixation member locking plate of FIG. 19A.

FIG. 20 is an exploded ISO view of another variant of the intervertebral implant of FIG. 16 with a non-limiting representative bone fixation member locking plate and a non-limiting faceplate/spinal cage fixation plate.

FIG. 21 is an assembled ISO view of the intervertebral implant of FIG. 20.

FIG. 22A is a non-limiting exploded ISO view of another variant of the intervertebral implant of FIG. 3 with universal left (or right) bone fixation members.

FIG. 22B is a non-limiting assembled ISO view of the intervertebral implant of FIG. 22A.

FIG. 22C is a superior view of the intervertebral implant of FIG. 22B.

FIG. 22D is an inferior view of the intervertebral implant of FIG. 22B.

FIG. 23A is a non-limiting ISO view of a universal left (or right) bone fixation member.

FIG. 23B is a side view of the universal left (or right) bone fixation member of FIG. 23A.

FIG. 23C is a superior, slightly rotated view of the universal left (or right) bone fixation member of FIG. 23A.

FIG. 23D is an anterior view of the universal left (or right) bone fixation member of FIG. 23A.

FIG. 23E is a posterior view of the universal left (or right) bone fixation member of FIG. 23A.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
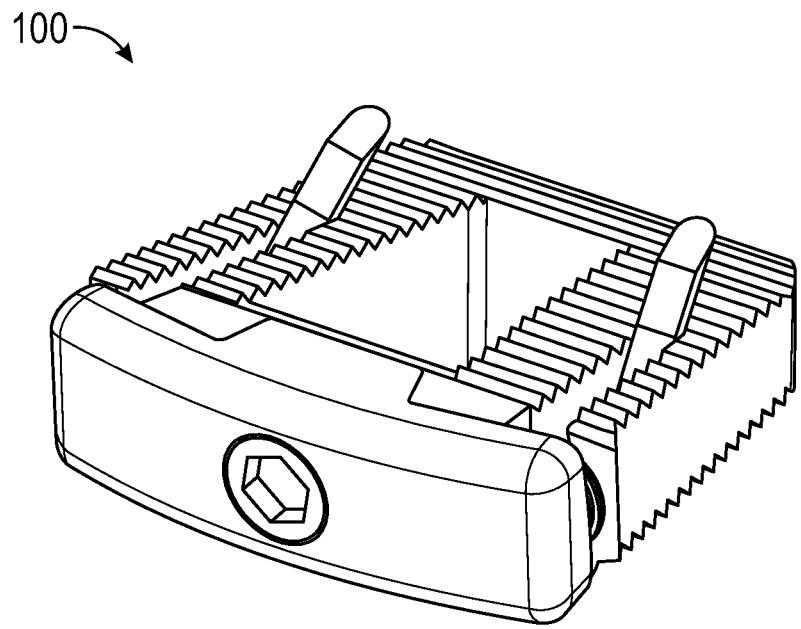
Figure 2:
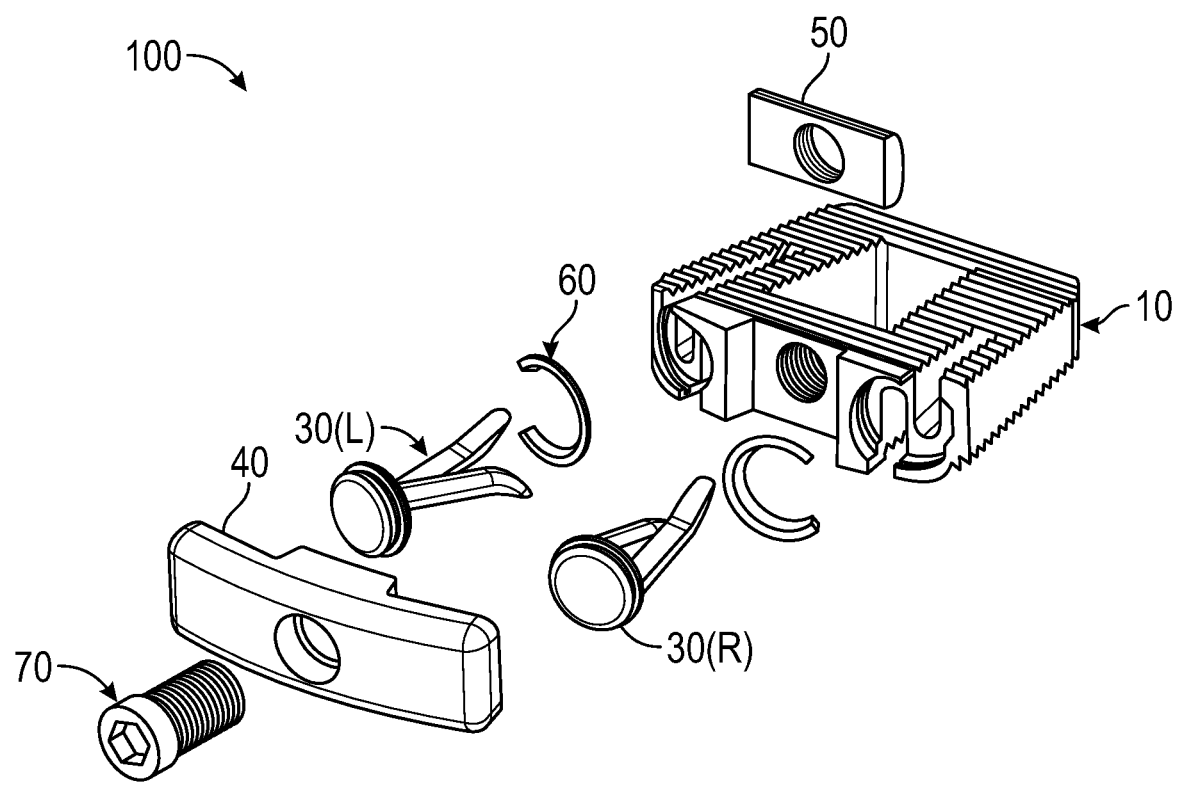
Figure 3:
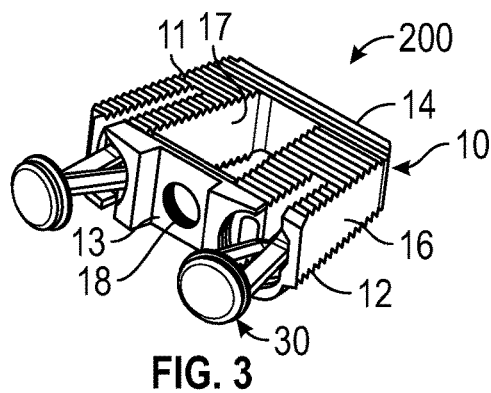

An implant and method for fusing adjacent spinal vertebra is disclosed. In an embodiment for a spinal implant of the present invention, the implant includes a spacer body assembly and two retention members. The two retention members each include split fork tangs wherein the tangs of each retention member are simultaneously extendable from the spacer body assembly into the adjacent vertebra. A method of fusing adjacent vertebrae includes the step of inserting an implant between adjacent vertebrae with retention members. The method also includes the step of configuring the retention members wherein a portion of each tang of a retention member simultaneously extends from the implant into one of the adjacent vertebra.

Spinal fixation systems such as pedicle screw and rod constructs are commonly used to promote fusion between intervertebral bodies. The insertion of pedicle screws typically requires a linear "line-of-approach" trajectory that is aligned with the longitudinal axis of the screw, in order to accommodate the access and delivery instruments. Similarly, anchors such as bone screws may be used to directly fix intervertebral implants to vertebral bodies, typically requiring the insertion of several screws at unique angles oblique to the sagittal and/or transverse plane, and thus multiple lines-of-approach. However, in a variety of surgical situations, achieving a desired trajectory for screw insertion can be difficult due to the patient's anatomy obstructing a linear line-of-approach. What is therefore desirable are spinal fixation systems that allow for the creation of rigid constructs when the linear line-of-approach for insertion of fixation anchors is unavailable and/or undesirable (e.g., when multiple anchors are required), while at the same time providing increased rigidity and robustness to spinal constructs such as those used in unilateral fusion procedures.

Provided herein is an intervertebral implant for positioning between a first vertebra and a second vertebra successive to the first vertebra, the intervertebral implant comprising a singular spacer body comprising; a superior surface configured to contact an inferior endplate of the first vertebra, an inferior surface configured to contact a superior endplate of the second vertebra, an anterior wall, a posterior wall, a first lateral wall extending between the posterior wall and the anterior wall, a second lateral wall extending between the posterior wall and the anterior wall, and an interior graft window defined by the anterior wall, the posterior wall, the first lateral wall and the second lateral wall, the interior graft window comprising; a graft aperture open to either the superior surface, the inferior surface or both the superior surface and the inferior surface, a first split-guide in the anterior wall, the first split-guide comprising: a first ramped channel extending from the anterior surface to the superior surface within the first lateral wall; and a second ramped channel extending from the anterior surface to the inferior surface within the same first lateral wall.

Referring now to FIGS. 1, 2, 3 and 4A-4C are various embodiments of an intervertebral implant as previously described herein. FIGS. 1, 2, 3 and 4A-4C illustrate one such embodiment 100 having a spacer body 10, comprising; a superior surface 11 configured to contact an inferior endplate of the first vertebra, an inferior surface 12 configured to contact a superior endplate of the second vertebra, an anterior wall 13, a posterior wall 14, a first lateral wall 15 extending between the posterior wall 14 and the anterior wall 13, a second lateral wall 16 extending between the posterior wall 14 and the anterior wall 13, and an interior graft window 17 defined by the anterior wall, the posterior wall, the first lateral wall and the second lateral wall. The interior graft window 17 is configured such that a graft aperture is open to either the superior surface 11, the inferior surface 12, or both the superior surface 11 and the inferior surface 12. Further, the spacer body comprises a first split guide aperture 20 comprising a first ramped channel 22 extending from the anterior surface 13 to the superior surface 11 within the first lateral wall 15, and a second ramped channel 23 extending from the anterior surface 13 to the inferior surface 12 within the same first lateral wall 15.

In some embodiments, the intervertebral implant 100 further comprises a first bone fixation member 30, also called a retainer, as illustrated in FIGS. 5A-5E and 6A-6E, and comprises: a cap 35 with an anterior surface 31 and posterior surface 32; a capture feature 36 on the cap; a first retention tang, (or simply, tang), 33 and a second retention tang 34 forming a split-fork configuration; wherein the first retention tang 33 and second retention tang 34 protrude from the posterior face 32 of the cap.

In some embodiments, the bone fixation member/retainer 30 is provided in a left-hand configuration 30L, a right-hand configuration 30R, or both 30L & 30R. As illustrated herein, the right-hand configuration 30R, as illustrated in FIGS. 5A-5E, provides for a first tang 33 that is elevated superiorly on the right side when viewed from the anterior face of the cap feature 35 and the second tang 34 is pointing divergently in an inferior direction. Alternatively, the bone fixation member/retainer 30 is also provided in a left-hand configuration 30L, as illustrated in FIGS. 6A-6E. The left-hand configuration 30L, provides for a first tang 33 that is elevated superiorly on the left side when viewed from the anterior face of the cap feature 35 and the second tang 34 is pointing divergently in an inferior direction.

As illustrated in FIGS. 3, 4A-4C and 5A-5E, a first left hand bone fixation member/retainer 30L is configured to be inserted through the first split-guide 20 wherein the first ramped channel 22 is configured to guide the first retention tang 33 toward the first opening 24 in the anterior surface 11 and the second ramped channel 23 is configured to guide the second retention tang 34 toward the second opening 25 in the inferior surface 12. As one of skill in the art will recognize, the orientation of the tangs and ramped channels can easily be reversed to accommodate a right-handed configuration.

Figure 14:
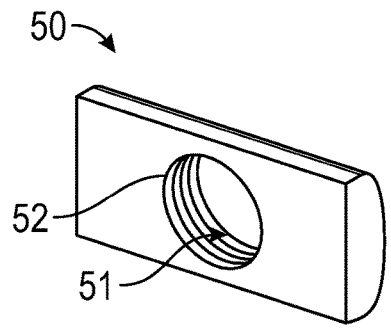
Figure 15A:
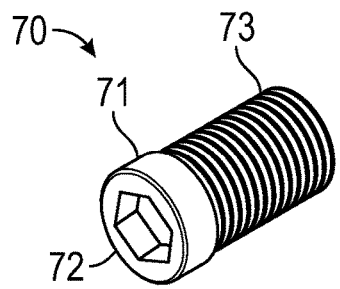
Figure 15B:
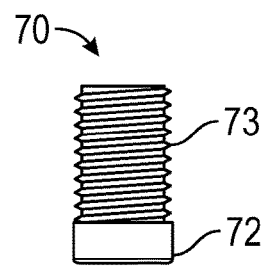
Figure 16:
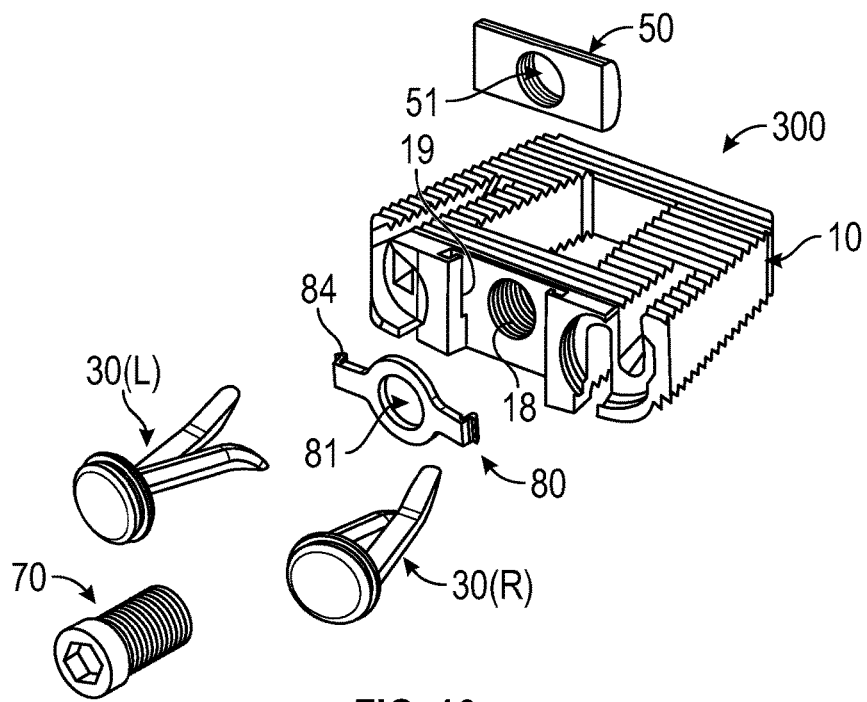
Figure 17A:
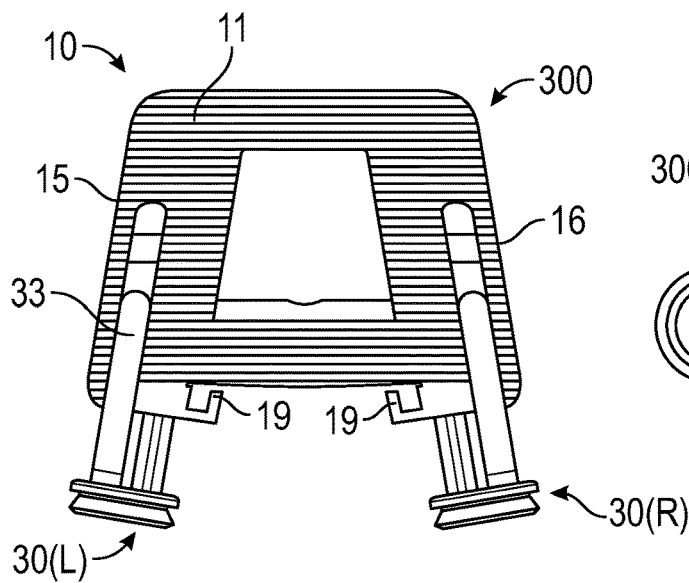
Figure 17B:
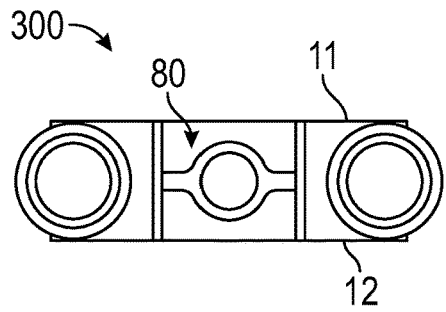
Figure 17C:
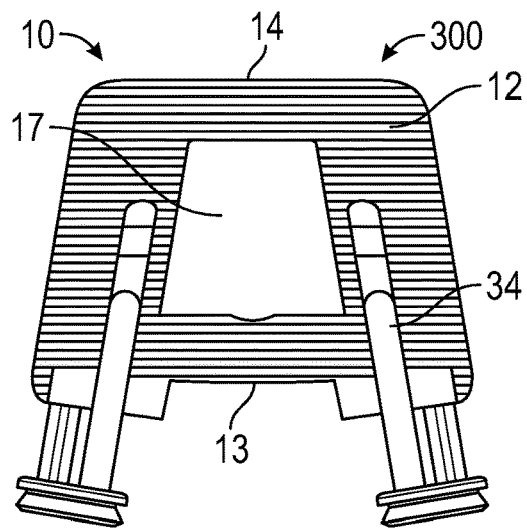
Figure 18A:
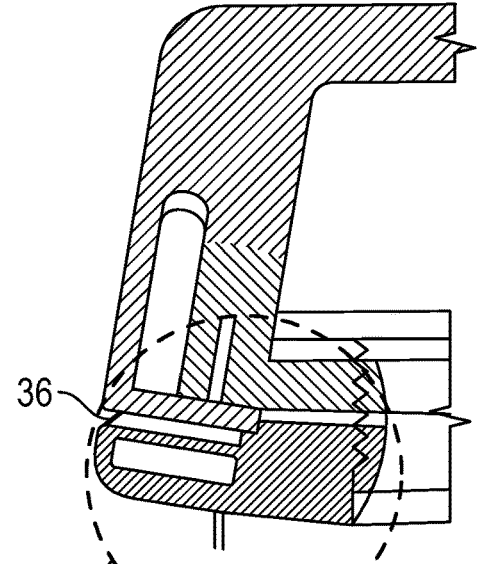
Figure 18B:
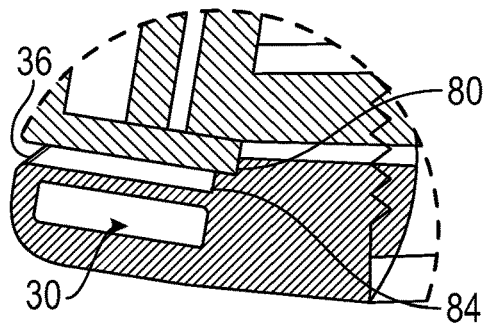
Figure 19A:
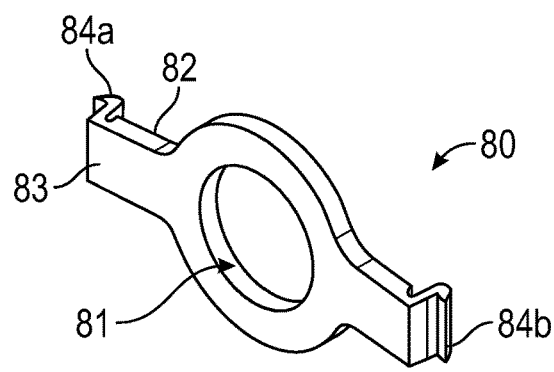
Figure 19B:
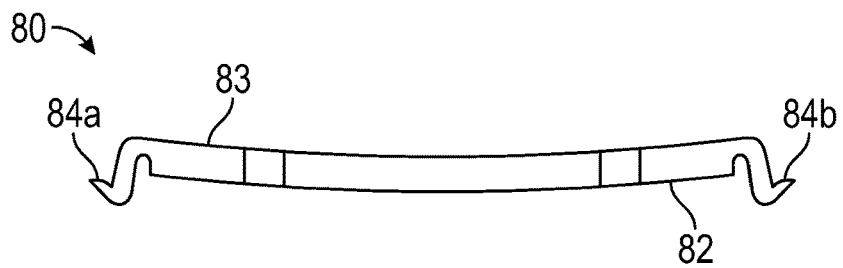
Figure 19C:
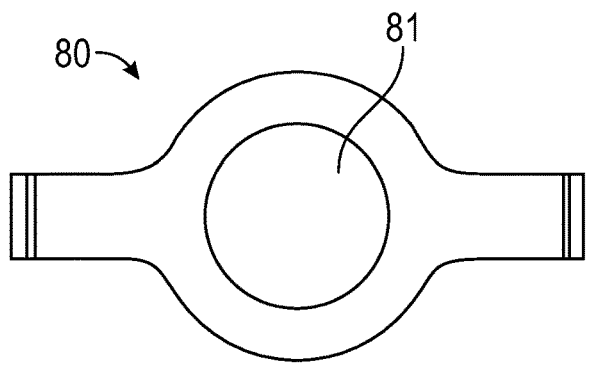
Figure 19D:
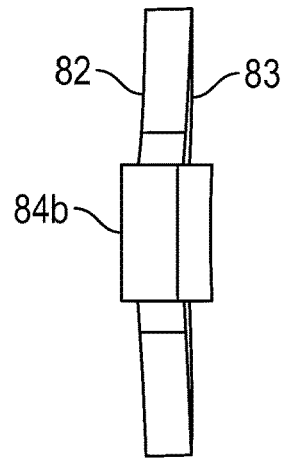
Figure 20:
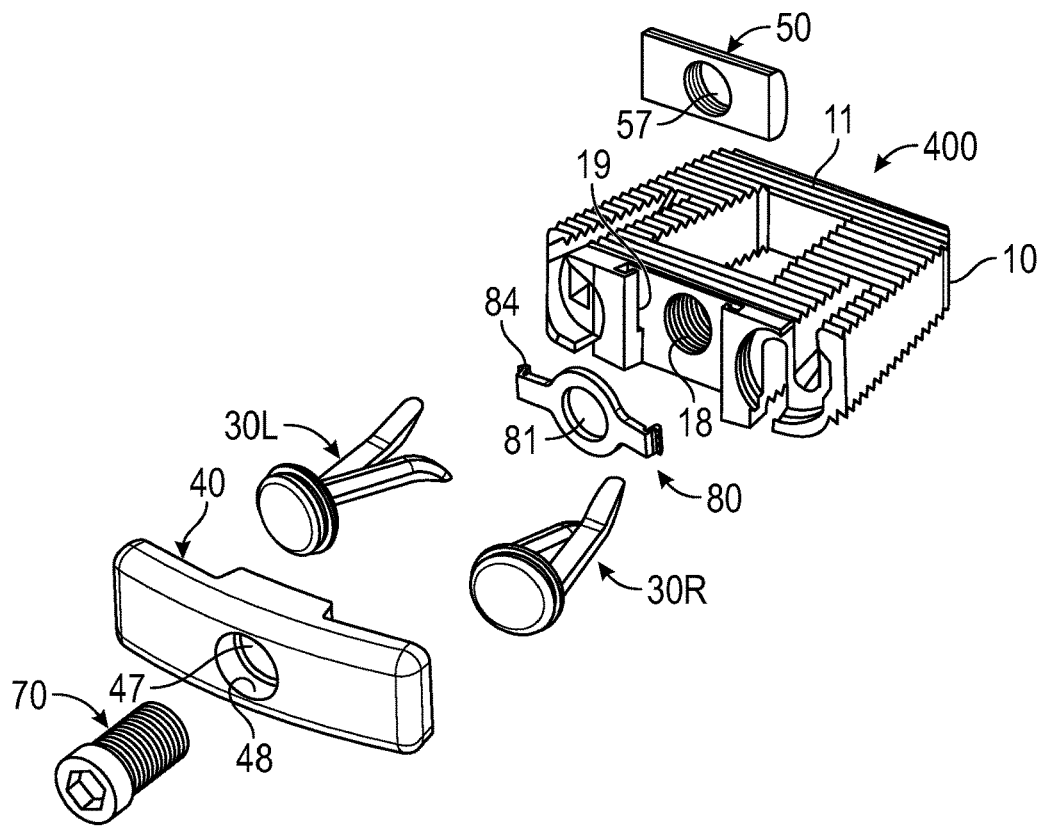
Figure 21:
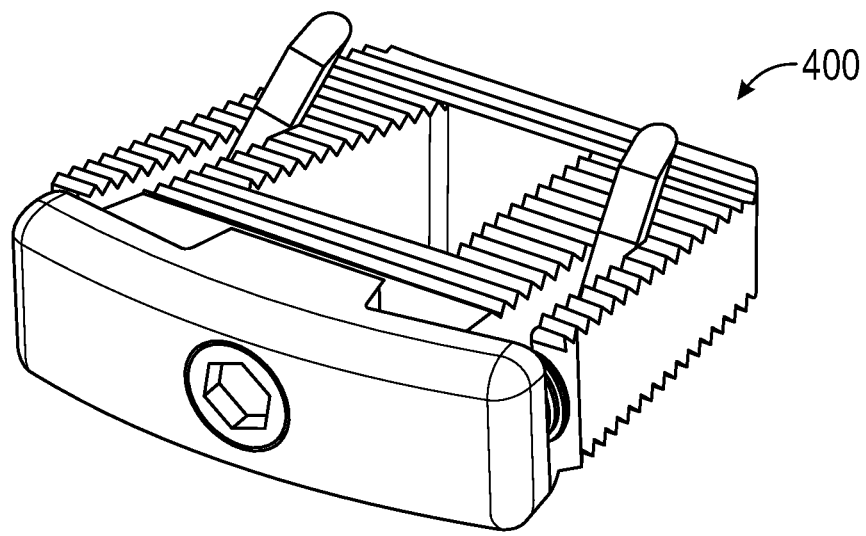
Figure 22A:
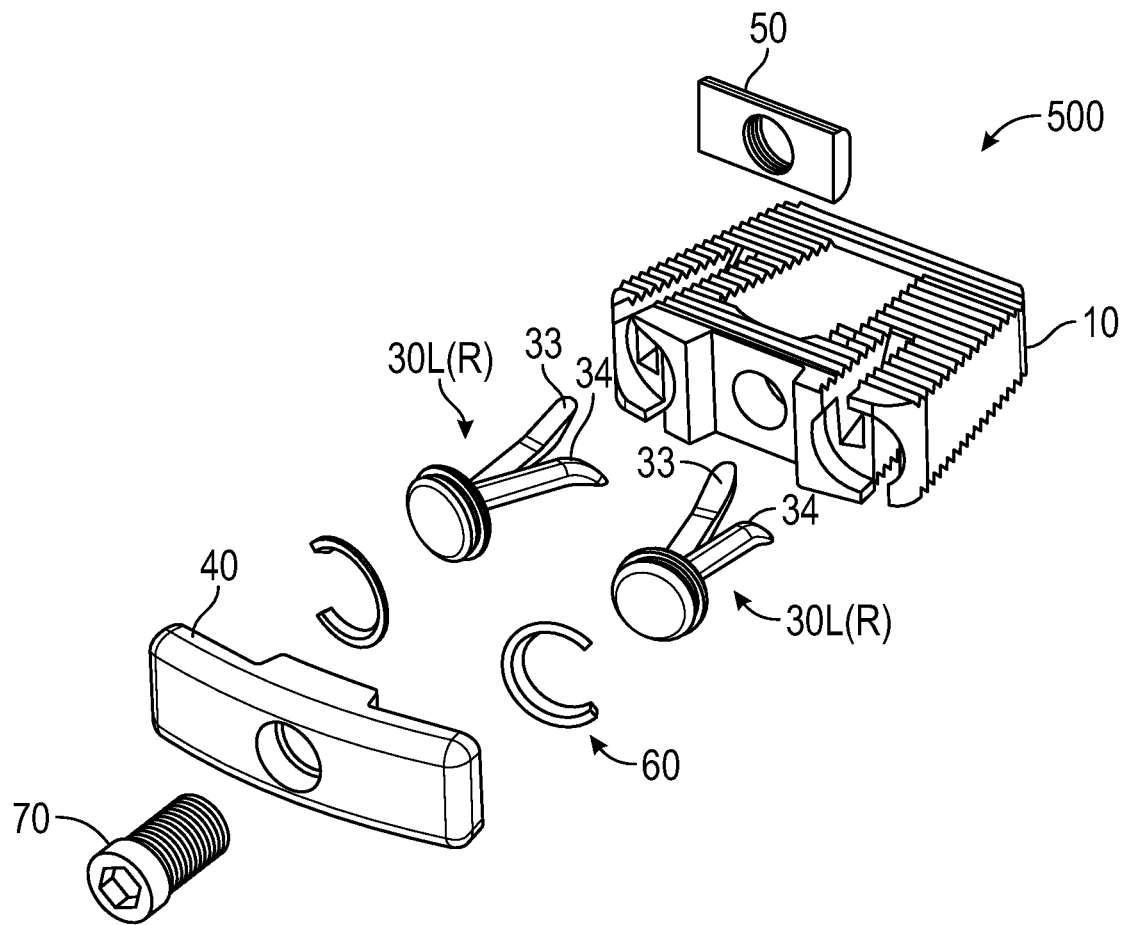
Figure 23C:
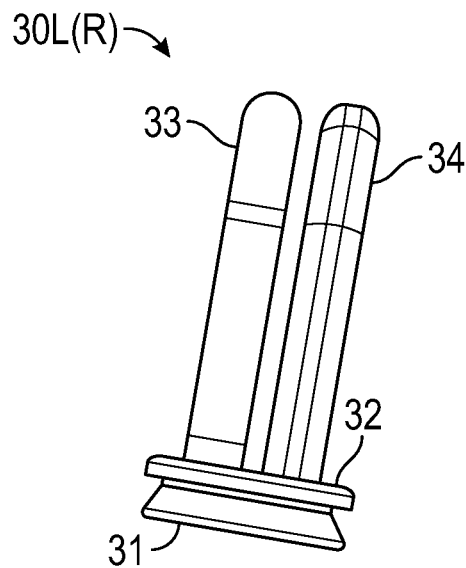
Figure 23D:
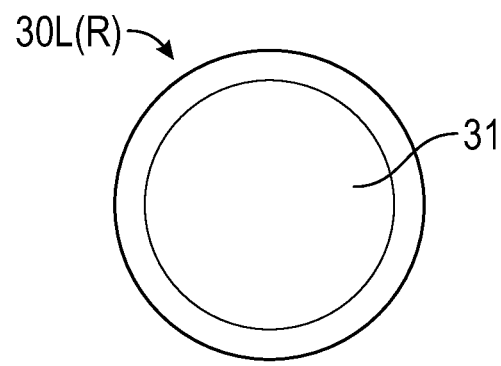
Figure 23E:
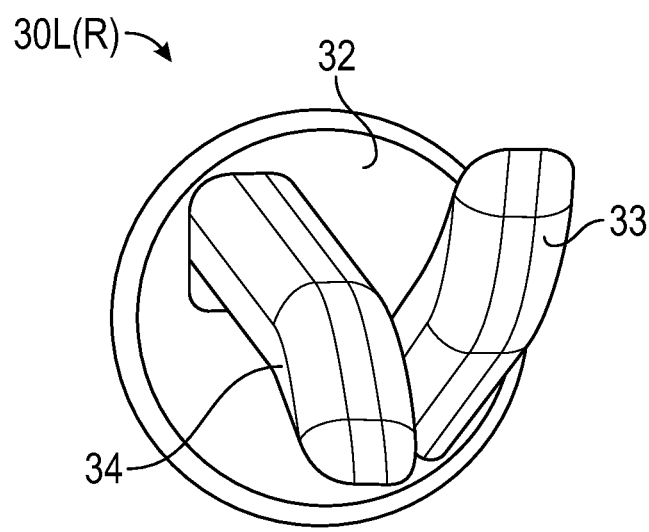

In some embodiments, the intervertebral implant 100 further comprises a first fixation aperture 18 in the anterior wall 13 extending to the interior graft window 17 and an insert plate 50 configured to be coupled to the spacer body 10 within the interior graft window 17. The insert plate 50 comprises a second fixation aperture 51 extending therethrough, as illustrated in FIG. 14, and is configured to coaxially align with the first fixation aperture 18. In a typical embodiment, the first fixation aperture and the second fixation aperture are configured to receive a locking mechanism. Typically, either the first or second fixation aperture is configured with a feature 52 for securing an attachment mechanism such as a screw, a bolt, a pin, a bayonette connection or the like. Those features 52 would include threads, grooves, tapers or other comparable fixation features.

Figure 4A:
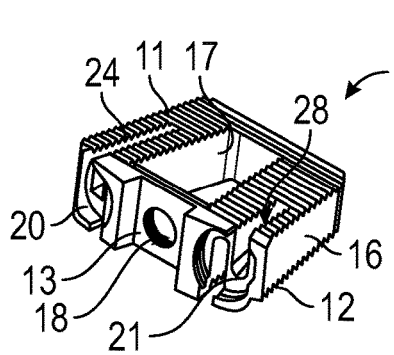
Figure 4B:
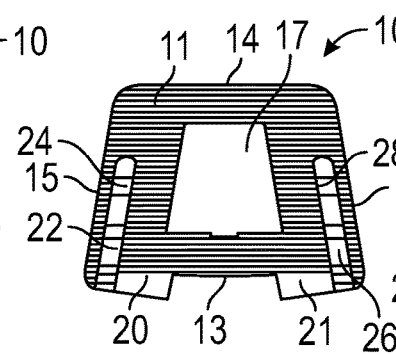
Figure 4C:
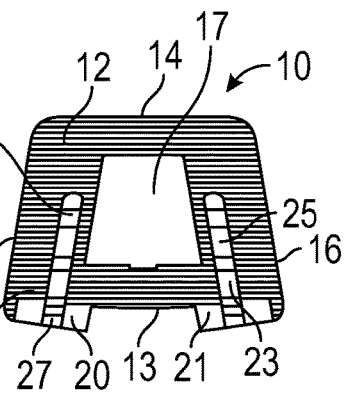
Figure 5A:
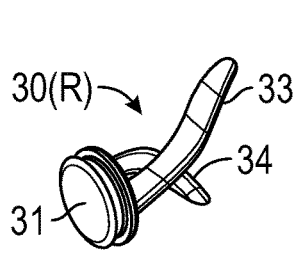
Figures 5B, 5C:
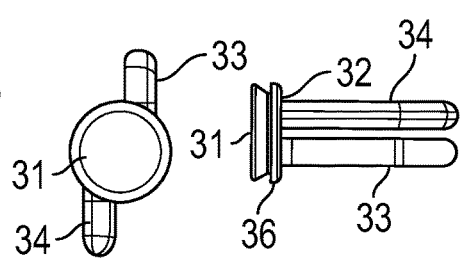
Figure 5D:
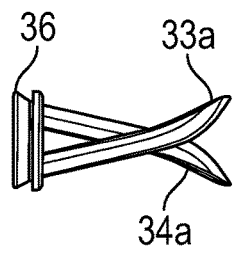
Figure 5E:
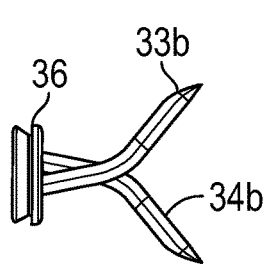
Figure 6A:
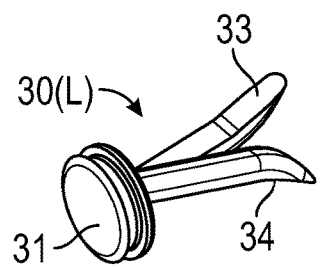
Figures 6B, 6C:
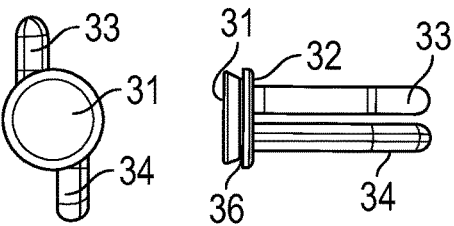
Figure 6D:
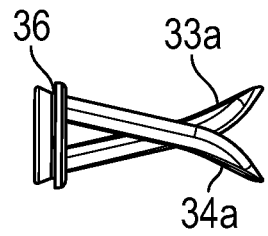
Figure 6E:
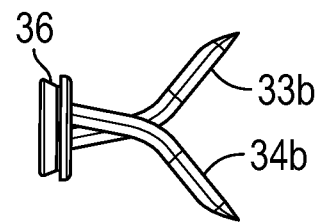
Figure 7A:
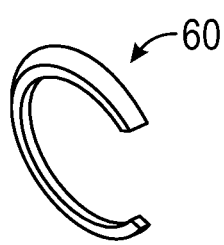
Figure 7B:
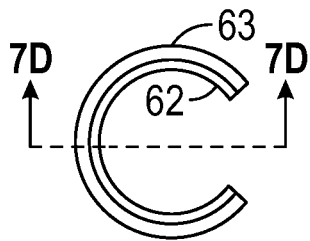
Figure 7C:
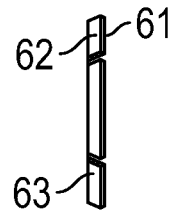
Figure 7D:
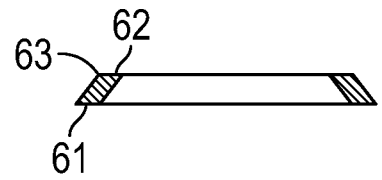
Figure 8A:
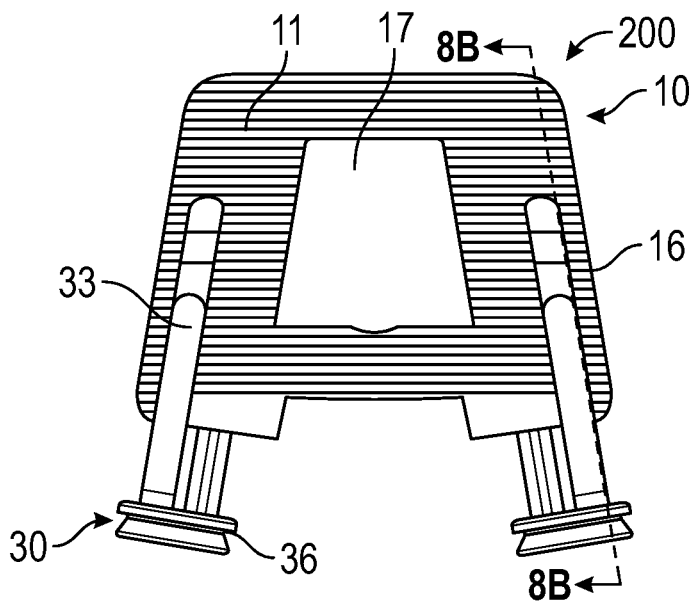
Figure 8B:
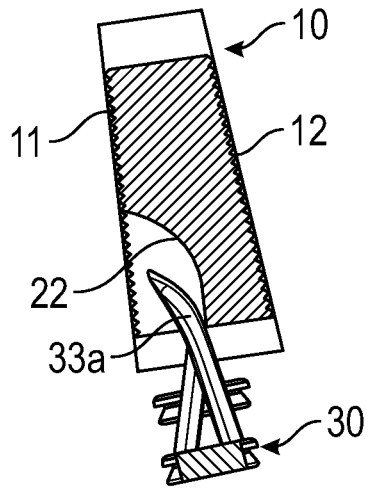
Figure 8C:
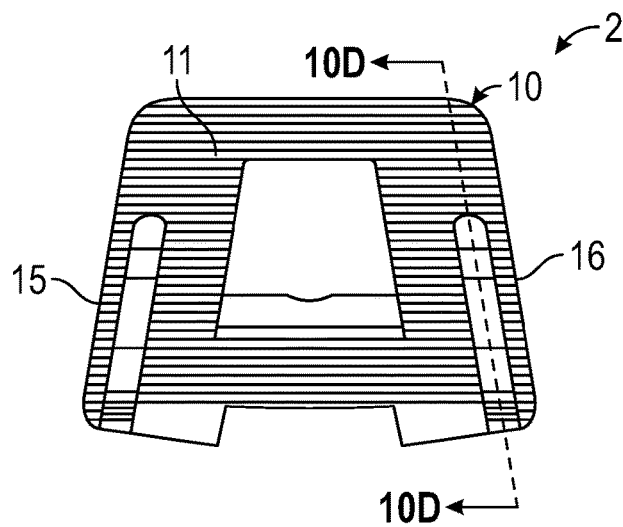
Figure 8D:
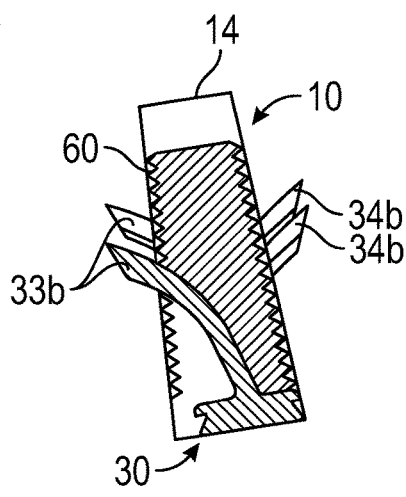
Figure 9:
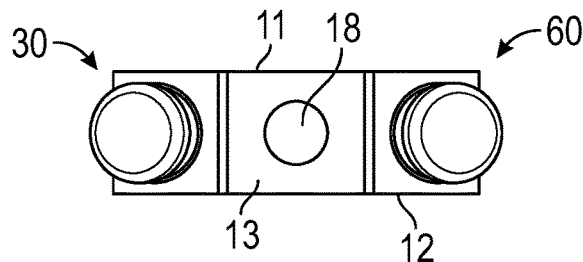
Figure 10A:
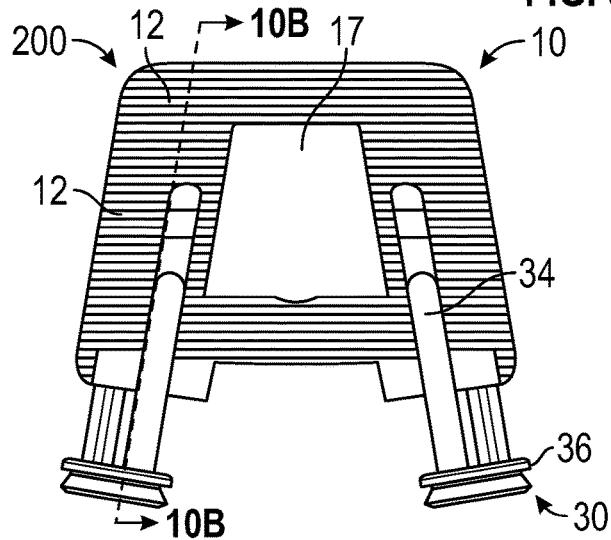
Figure 10B:
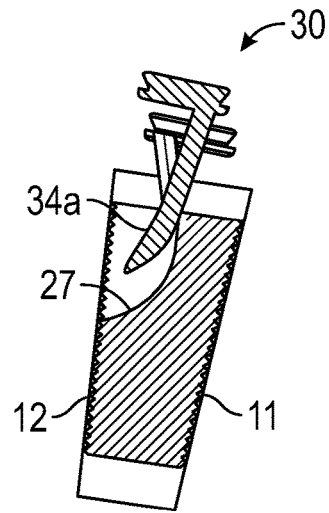
Figure 10C:
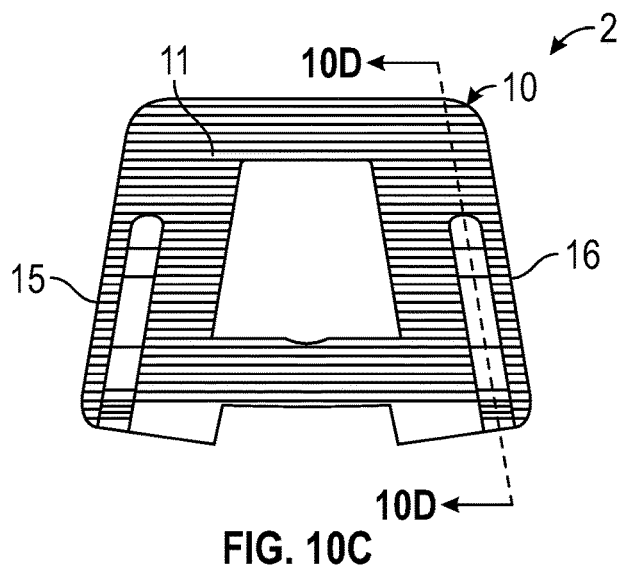
Figure 10D:
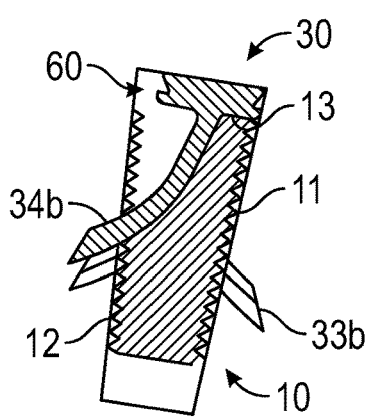
Figure 11:
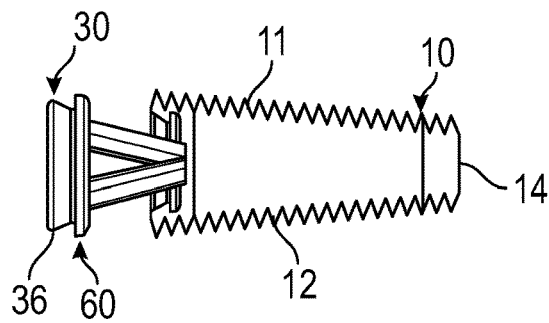
Figure 12:
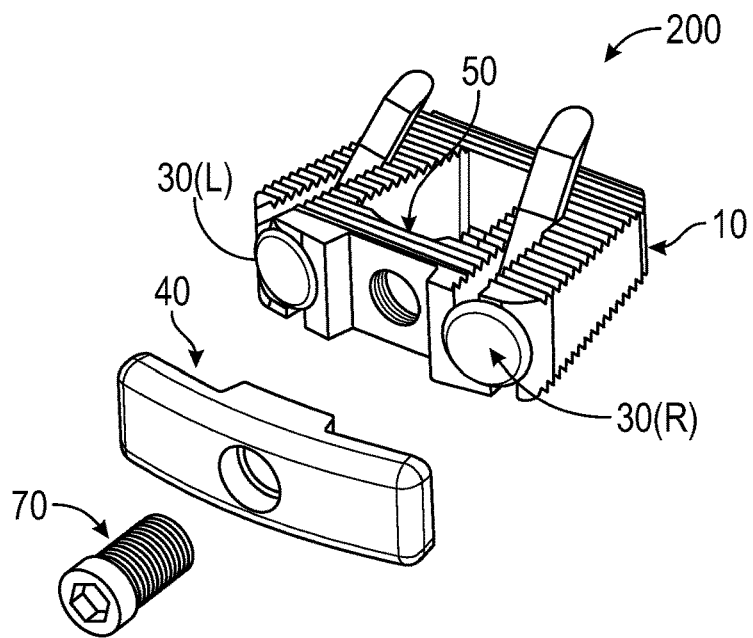
Figure 13A:
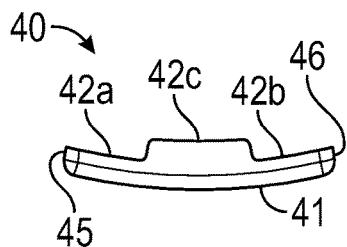
Figure 13B:
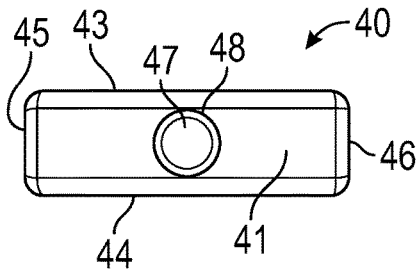
Figure 13C:
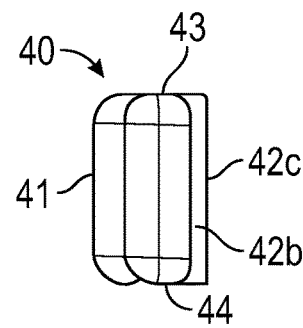

As further illustrated in FIGS. 4A-4C, some embodiments of the intervertebral implant 100 further comprise a second split-guide 21 in the anterior wall 13, the second split-guide comprising: a third ramped channel 26 extending from the anterior surface 13 to the superior surface 11 within the second lateral wall 16; and a fourth ramped channel 27 extending from the anterior surface 13 to the inferior surface 12 within the same second lateral wall 16.

In some embodiments, the intervertebral implant further comprises a second bone fixation member/retainer 30R comprising: a cap 35 with an anterior 31 and a posterior 32 surface; a capture feature on the cap 36, a third retention tang 33 and fourth retention tang 34, also forming a split fork configuration; wherein the third retention tang and fourth retention tang protrude from the posterior face 32 of the cap. The right-hand configuration 30R, as illustrated in FIGS. 5A-5E, provides for a first tang 33 that is elevated superiorly on the right side when viewed from the anterior face 31 of the cap feature 35 and the second tang 34 is pointing divergently in an inferior direction.

In some embodiments, the second bone fixation member/retainer 30R is configured to be inserted through the second split-guide 21 wherein the third ramped channel 26 is configured to guide the third retention tang 33 toward the third opening 28 in the anterior surface 11 and the fourth ramped channel 27 is configured to guide the fourth retention tang 34 toward the fourth opening 29 in the inferior surface 12.

In some embodiments, the first and/or second split-guide 20, 21 is configured to receive the first and/or second bone fixation member/retainer 30R, 30L comprising a cap 35 with two retention tangs 33, 34 and provide a guided pathway to simultaneously direct the two retention tangs in opposite directions such that when the bone fixation member/retainer is impacted, the first of two tangs 33 (L & R) at least partially penetrates the inferior endplate of the adjacent superior vertebra and the second of two tangs 34 (L&R) simultaneously, at least partially penetrates the superior endplate of the adjacent inferior vertebra.

In some embodiments, the bone fixation member/retainer each comprising two retention tangs 33, 34, each retention tang having a first end "x", a lengthwise body "z" and a second end "z" opposite the first end and having the split-fork configuration relative to each other are configured such that the tangs protrude from the cap, wherein the first end "x" of each retention tang is affixed to and protruding from the posterior surface 32 of the cap 35, each retention tang in a plane parallel to the other retention tang, and wherein the second end "y" of each retention tang is oriented at a non-perpendicular angle to the posterior surface 32 of the cap 35 and each second end "y" is oriented in divergent directions to the other retention tang.

In some embodiments, each retention tang of the bone fixation member is configured such that the lengthwise body "z" of each retention tang is: straight; arcuate or helical between the first end "x" and the second end "y".

In some embodiments, the first or second split-guide 20, 21 comprises a first of two ramped channels 22, 26 having a first end at the split-guide anterior face aperture, a lengthwise pathway and a second end providing an opening 24, 28 to the superior surface 11 within a lateral wall 15, 16; and a second of two ramped channels 23, 27 having a first end at the split-guide anterior face aperture, a lengthwise pathway and a second end providing an opening 25, 29 to the inferior surface 12 within the same lateral wall 16; wherein each ramped channel lengthwise pathway is shaped such that the configuration of the lengthwise pathway is: straight, arcuate or helical between the first end and the second end of each respective ramped channel. The configuration of the split guide and ramped channels is configurable for either left-handed retainers, right-handed retainers, or both left and right-handed retainers.

In some embodiments of the intervertebral implant, the orientation of the ramp channels is reversed, creating a right-handed orientation, wherein the first opening in the first ramped channel is in the inferior surface of the first lateral wall, the second ramped opening is in the anterior surface of the of the first lateral wall, the third opening in the third ramped channel is in the inferior surface of the second lateral wall and the fourth ramped opening is in the anterior surface of the of the second lateral wall.

In some embodiments the intervertebral implant comprises both left-hand orientation ramp channels and right-hand orientation ramp channels.

In some embodiments, at least one of the two retention tangs 33, 34 further comprises a plurality of substantially inversely shaped "V" notches (not shown) along the lengthwise body "z", anywhere between a middle of the lengthwise body and proximate to the second end 'z", wherein the plurality of notches are configured to promote resistance to extraction of the retention tang and the overall bone fixation member/retainer from a vertebral bone or the spacer body from the intervertebral space after insertion.

In some embodiments, a tip on the second end "z" of each retention tang 33, 34 is configured to penetrate: a vertebral endplate, a cancellous bone or a cortical bone of a vertebra.

In some embodiments, the bone fixation member 30 comprising helical retention tangs 33, 34 along the lengthwise body "z" of the tang, configured to at least partially penetrate the inferior endplate of the superior adjacent vertebra and simultaneously, at least partially penetrate the superior endplate of the inferior adjacent vertebra in a corkscrew manner such that each tang follows a helical path unique to the helix of each retention tang and wherein the entire bone fixation member/retainer 30 rotates as it is deployed through the ramped channels 22, 23, 26, 27 of the spacer body 10.

In some embodiments, the bone fixation member 30 comprises a left-handed orientation 30L, as illustrated in FIGS. 6A-6E, wherein the second end "z" of a left retention tang 33 is oriented superiorly at a non-perpendicular angle to the posterior surface 32 of the cap 35 and the second end "z" of a right retention tang 34 is oriented inferiorly at a non-perpendicular angle to the posterior surface 32 of the cap 35 and each second end "z" of the left and right retention tang 33, 34 is oriented in a divergent direction to the other retention tang.

In some embodiments, the intervertebral implant 100, 200, 300, 400 further comprises both a left-handed orientation bone fixation member/retainer 30L and a right-handed orientation bone fixation member/retainer 30R when fully assembled, as illustrated in FIGS. 1, 2, 3, 12, 16, 20 and 21.

In some embodiments, the intervertebral implant 500 further comprises only a left-handed orientation bone fixation member/retainer 30L or a right-handed orientation bone fixation member/retainer 30R when fully assembled, as illustrated in FIGS. 22A-22D.

In some embodiments, the bone fixation member/retainer 30 with helical retention tangs comprises a left-handed orientation, wherein the helix is left-handed. In some embodiments, the bone fixation member/retainer 30 with helical retention tangs comprises a right handed orientation, wherein the helix is right-handed.

In some embodiments, the bone fixation member/retainer 30 comprises a right handed orientation, wherein the helix is right-handed, such that the second end "z" of a right retention tang 33 is oriented superiorly at a non-perpendicular angle to the posterior surface 32 of the cap 35 and the second end "z" of a left retention tang 34 is oriented inferiorly at a non-perpendicular angle to the posterior surface 32 of the cap 35 and each second end "z" of the right and left retention tang 33, 34 is oriented in a divergent helical direction to the other retention tang.

In some embodiments of the intervertebral implant the orientation of the ramp channel 22, 23, 26, 27 is helical, wherein the first opening 24 in a first ramped helical channel 22 is in the inferior surface 12 of the first lateral wall 15, the second ramped opening 25 in a second ramped helical channel 23 is in the superior surface 11 of the of the first lateral wall 15, the third opening 28 in the third ramped helical channel 26 is in the inferior surface 12 of the second lateral wall 16 and the fourth ramped opening 29 in the fourth ramped helical channel 27 is in the superior surface 11 of the of the second lateral wall.

In some embodiments, the intervertebral implant comprises a right handed helical orientation ramped channel, wherein the helix is right-handed. In some embodiments, the intervertebral implant comprises a left handed helical orientation ramped channel, wherein the helix is left-handed. In still other embodiments, the intervertebral implant comprises both a left-handed and a right-handed helical ramp channel.

In some embodiments, the intervertebral implant further comprises a retaining clip 60 configured figured to capture the bone fixation member 30 within the opening of the first or second split-guide 20, 21.

In some embodiments, the intervertebral implant further comprises a retaining clip 60 configured to capture the bone fixation member 30 within the split-guide aperture. As illustrated in FIGS. 5A-5E and 6A-6E, a non-limiting example of a capture feature 36 is illustrated in the cap 35 of the bone fixation member/retainer 30 (L&R).

As illustrated in FIGS. 1, 2, 12, 13A-13C, 20, 21 and 22A-22C some embodiments of the intervertebral implant further comprises a faceplate 40 or spinal cage fixation plate and a locking mechanism 60, 80; wherein the faceplate or spinal cage fixation plate 40 comprises an anterior face 41, a stepped posterior face 42a-42c, top edge 43, a bottom edge 44 spaced apart from the top edge, a first lateral edge 45 and a second lateral edge 46, wherein the faceplate or spinal cage fixation plate further comprises a third fixation aperture 47 extending therethrough and a counter-bore 48, both the third fixation aperture 47 and the counter-bore 48 configured to coaxially align with the first 18 and second fixation aperture 51, wherein the locking mechanism 70 is configured to pass through the third fixation aperture 47 and into the first 18 and second fixation apertures 18 to securely retain the faceplate or spinal cage fixation plate 40 against the anterior wall 13 of the spacer body 10, and wherein a locking mechanism head or cap 71 is captured within the counter-bore 48.

In some embodiments the locking mechanism is a clip or retaining ring 60 as illustrated in FIGS. 7A-7D; comprising an anterior face 61, a posterior face 62, a leading edge or chamfer 63 to facilitate compression into a retaining groove on the spacer body or into the capture groove 36 of the bone fixation member/retainer 30.

In some embodiments of the intervertebral implant, the locking mechanism is a locking plate 80 as illustrated in FIGS. 16, 17A-17C, 18A, 18B, 19A-19D and 20; comprising an anterior face 82, a posterior face 83, at least one capture tang 84 to facilitate capturing and holding the retaining groove on the bone fixation member/retainer 30 and/or into a capture groove 19 on the anterior face of the spacer body. The locking plate is also configurable with multiple capture tangs (i.e.: 84a, 84b, etc.) capable of capturing and holding multiple retaining grooves on multiple bone fixation members/retainers 30 and/or multiple capture grooves 19 on the anterior face of the spacer body. Further still, the locking plate is configured with a $4^{th}$ fixation aperture, configurable to accept a fixation member (i.e.: screw, bolt, pin, etc.) and be constrained to the anterior face of the spacer body through the 1$^{st}$, second and/or 3$^{rd}$ fixation aperture.

As illustrated in FIGS. 16, 17A-17C, 18A, 18B and 20, the locking plate locking mechanism can be used with or without a faceplate or spinal cage fixation plate 40.

In some embodiments, the faceplate or spinal cage fixation plate 40 is further configured to be a secondary capture mechanism for at least the first bone fixation member/retainer 30, to prevent unintentional removal thereof.

In some embodiments, the first and second bone fixation member each comprising two retention tangs, are provided with the faceplate or spinal cage fixation plate 40 for delivery to a spacer body 10 such that the faceplate or spinal cage fixation plate 40 comprises recesses in the posterior faces 42a and 42c, and further comprise retention grooves to securely hold a bone fixation member 30 fitted with a retaining clip affixed to the capture groove 36 in the cap 35.

In some embodiments, the first and second bone fixation member each co/retainer 30 comprising two retention tangs 33, 34, are provided with the spacer body 10, inserted at least partially into the first and second split-guide aperture 20, 21, wherein the first, second, third and fourth tangs 33, 34 are in a compressed, non-deployed state 33a, 34a, as illustrate in FIGS. 3, 5D, 6D, 8B and 10B.

In some embodiments, the first and second bone fixation member each comprising two retention tangs, are provided with the faceplate in an orientation configured to match that of the channels in the split-guides.

In some embodiments, the first, second, third and fourth tangs 33, 34 become decompressed 33b, 34b, as illustrated in FIGS. 5E, 6E 8D and 10D, and at least partially penetrate the adjacent vertebra when the first and second bone fixation members/retainers 30 are pushed fully into the first and second split-guide openings 20, 21.

In some embodiments, the locking mechanism 70 comprises: a screw; a bolt; a bayonette connection; a pin; a tapered pin or a split-compression pin. In some embodiments the locking mechanism 70 further comprises a "head-driving" feature, such as a screw driver groove, or an Allen wrench socket, etc., to name just a few non-limiting examples.

Provided herein is a method of fusing a first vertebra and a second vertebra successive to the first vertebra, comprising the steps of: inserting a spacer body 10 between prepared facing surfaces of the first vertebra and a second vertebra, the spacer body 10 comprising a superior surface 11, an inferior surface 12 and an interior graft window 17 defined by an anterior wall 13, a posterior wall 14, a first lateral wall 15, and a second lateral wall 16; inserting a first retainer 30 in a compressed configuration 33a, 34a into a first split-guide aperture 20 extending from the anterior wall 13 into the first lateral wall 15 of the spacer body, the first retainer 30 comprising a first tang 33 and a second tang 34, said first and second tangs comprising a split-fork configuration relative to one another; driving the first retainer fully into the first split-guide aperture such that the first tang 33 engage a first ramped channel 22 and extends out of a first opening 24 on the superior surface 11 of the first lateral wall 15 and the second tang 34 simultaneously engages a second ramped channel 23 and extends out of a second opening 25 on the inferior surface 12 of the first lateral wall 15; and wherein the first tang 33 is configured to at least partially penetrate the first adjacent vertebra and simultaneously, the second tang 34 is configured to at least partially penetrate the second adjacent vertebra, creating a decompressed configuration 33b, 34b for the first tang 33 and the second tang 34.

In some embodiments, the method comprises inserting a second retainer 30 in a compressed configuration 33a, 34a into a second split-guide aperture 21 extending from the anterior wall 13 into the second lateral wall 16 of the spacer body 10, the second retainer 30 comprising a third tang 33 and a fourth tang 34, said third and fourth tangs comprising a split-fork configuration relative to one another; driving the second retainer fully into the second split-guide aperture 21 such that the first tang 33 engages a third ramped channel 26 and extends out of a third opening 28 on the superior surface 11 of the second lateral wall 16 and the fourth tang 34 simultaneously engages a fourth ramped channel 27 and extends out of a fourth opening 29 on the inferior surface 12 of the second lateral wall 16; and wherein the third tang 33 is configured to at least partially penetrate the first adjacent vertebra and simultaneously, the second tang 34 is configured to at least partially penetrate the second adjacent vertebra, creating a decompressed configuration 33b, 34b for the third tang 33 and the fourth tang 34.

In some embodiments, the method optionally comprises the step of inserting a bone graft material into the graft window 17 prior to inserting the spacer body 10 between the prepared surfaces of the first and second adjacent vertebra.

In some embodiments, the method further comprises the steps of: optionally affixing a faceplate or spinal cage fixation plate 40 to an anterior surface 13 of the spacer body 10 and securing said faceplate or spinal cage fixation plate with a locking mechanism 70; wherein the faceplate or spinal cage fixation plate 40 is configured to be a secondary capture mechanism for the first and second retention members.

In some embodiments, the method further comprises the steps of: optionally affixing a faceplate or spinal cage fixation plate 40 comprising at least one fixation spike (not shown), wherein the at least one fixation spike is positioned superiorly to the superior surface of the fixation plate and configured to temporarily secure the fixation plate to a superior adjacent vertebra.

In some embodiments, the method still further comprises the steps of: optionally affixing a faceplate or spinal cage fixation plate 40 comprising at least a second fixation spike, (not shown); wherein the at least second fixation spike is positioned inferiorly to the inferior surface of the fixation plate and configured to temporarily secure the fixation plate to an inferior adjacent vertebra.

In some embodiments, the method comprises the steps of: optionally affixing a faceplate or spinal cage fixation plate 40 comprising at least one aperture for receiving a bone screw (not shown), wherein the at least one aperture for receiving a bone screw is positioned superiorly to the superior surface of the fixation plate and configured to temporarily secure the fixation plate with a first screw to a superior adjacent vertebra.

In some embodiments, the method still further comprises the steps of: optionally affixing a faceplate or spinal cage fixation plate 40 comprising at least a second aperture for receiving a bone screw, (not shown); wherein the at least second aperture for receiving a bone screw is positioned inferiorly to the inferior surface of the fixation plate and configured to temporarily secure the fixation plate with a second screw to an inferior adjacent vertebra.

Provided herein is an intervertebral implant kit comprising: a spacer body 10 comprising; a superior surface 11, an inferior surface 12, and an interior graft window 17 defined by an anterior wall 13, a posterior wall 14, a first lateral wall 15, and a second lateral wall 16; and a first split-guide aperture 20 comprising: a first ramped channel 22 extending from the anterior wall 13 into the first lateral wall 15 and to a first opening 24 in the superior surface 11 of the first lateral wall 15; a second ramped channel 23 extending from the anterior wall 13 into the first lateral wall 15 and to a first opening 25 in the inferior surface 12 of the same first lateral wall 15; and a first recess at the anterior wall 20; and a first capture ring 60 configured to be placed in the first recess; wherein the superior surface 11 is configured to contact an inferior endplate of a first adjacent vertebra and the inferior surface 12 is configured to contact a superior endplate of a second adjacent vertebra, a first bone retainer 30 comprising: a first cap 30 with an anterior 31 and posterior 32 surface; a first tang 33; and a second tang 34 forming a split-fork configuration with the first tang; wherein the first tang 33 and second tang 34 both extend from the posterior surface 32 of the first cap 35, wherein the first tang and second tang initially both extend from the first cap in a plane generally parallel to each other and end at a first terminus "y" and a second terminus "y", respectively, and wherein the first terminus "y" of the first tang 33 is oriented at a non-perpendicular angle to the posterior surface 32 of the first cap 35 and the second terminus "y" of the second tang 34 is oriented at a non-perpendicular angle to the posterior surface 32 of the first cap 35 and is oriented in a divergent direction relative to the first terminus of the first tang, wherein the first tang and second tang of the first retainer comprise a compressed configuration 33a, 34a prior to delivery into the first split-guide aperture 20, and wherein upon delivery into the first split-guide aperture, the first and second tangs expand relative to one another 33b, 34b and are configured to at least partially penetrate the first adjacent vertebra and the second adjacent vertebra, respectively.

In some embodiments, the kit further comprises a second capture ring 60, a second retainer 30 comprising: a second cap 35 with an anterior 31 and posterior 32 surface; a third tang 33; and a fourth tang 34 forming a split-fork configuration with the first tang; wherein the third tang 33 and fourth tang 34 initially both extend from the second cap 35 in a plane generally parallel to each other, and end at a third terminus "y" and a fourth terminus "y", respectively, wherein the third terminus "y" of the third tang 33 is oriented at a non-perpendicular angle to the posterior surface of the second cap 35 and the fourth terminus "y" of the fourth tang 34 is oriented at a non-perpendicular angle to the posterior surface 32 of the second cap 35 and is oriented in a divergent direction relative to the third terminus of the third tang, and wherein the spacer body further comprises a second split-guide aperture 21 comprising: a third ramped channel 26 extending from the anterior wall 13 into the second lateral wall 16 and to a third opening 28 in the superior surface 11 of the second lateral wall 16; a fourth ramped channel 27 extending from the anterior wall 13 into the second lateral wall 16 and to a fourth opening 29 in to the inferior surface 12 of the second lateral wall 16; and a second recess 21 in the anterior wall 13, wherein the third tang 33 and fourth tang 34 of the second retainer 30 comprise a compressed configuration 33a, 34a prior to delivery into the second split-guide aperture 21, and wherein upon delivery into the second split-guide aperture, the third and fourth tangs expand 33b, 34b relative to one another and are configured to at least partially penetrate the first adjacent vertebra and the second adjacent vertebra, respectively.

In some embodiments, the first cap 35 and the second cap 35 are contiguous and/or are attached to one another. In some embodiments, the first cap 35 and the second cap 35 are integral to the faceplate or spinal cage fixation plate 40.

In some embodiments, the intervertebral implant kit further optionally comprises a faceplate or spinal cage fixation plate 40 and a locking mechanism 70; wherein the faceplate or spinal cage fixation plate 40 comprises a fixation aperture 47 extending therethrough and a counter-bore 48, both configured to coaxially align with a fixation aperture 18 in the spacer body, wherein the locking mechanism 70 is configured to pass through the faceplate fixation aperture 47, 48 and into the coaxially aligned spacer body fixation apertures 18, 51 to securely retain the faceplate 40 against the anterior wall 13 of the spacer body 10, wherein a locking mechanism head 71 or cap is captured within the counter-bore 84, and wherein the faceplate 40 is further configured to be a secondary capture mechanism for the first and second bone fixation members 30 (L&R) to prevent unintentional removal thereof.

Provided herein is an intervertebral implant 100, 200, 300, 400, 500 comprising: a singular spacer body 10 comprising a superior surface 11, an inferior surface 12, an anterior wall 13, a posterior wall 14, a first lateral wall 15 extending between the posterior wall 14 and the anterior wall 13, a second lateral wall 16 extending between the posterior wall 14 and the anterior wall 13, and an interior graft window 17 within the spacer body 10; wherein the superior surface 11 is configured to contact an endplate of a first adjacent vertebra and the inferior surface 12 is configured to contact an endplate of a second adjacent vertebra, and wherein the interior graft window 17 comprises at least one graft aperture open to either the superior surface, the inferior surface or both the superior and inferior surface, a first guide aperture 21 on the anterior wall 13, the first guide aperture comprising: a first ramped channel 22 providing a first opening 24 to the superior surface within the first lateral wall 15; and a second ramped channel 23 providing a second opening 25 to the inferior surface 12 within the same first lateral wall 15; a first bone fixation member 30 comprising a cap 35 with a first and second retention tang 33, 34 protruding therefrom configured to be inserted through the first guide aperture and at least partially penetrates the first adjacent vertebra and simultaneously, at least partially penetrates the second adjacent vertebra; wherein the bone fixation member 30 comprises a split fork configuration, a second bone fixation member 30 comprising: a cap 35 with an anterior 31 and posterior 32 surface; a third retention tang 33 and a fourth retention tang 34 forming a split-fork configuration; wherein the third retention tang and fourth retention tang protrude from the posterior face 32 of the cap 35, wherein the second bone fixation member is configured to be inserted through a second split-guide aperture 21 wherein the third ramped channel 26 is configured to guide the third retention tang toward the third opening 28 in the superior surface 11 and the fourth ramped channel 27 is configured to guide the fourth retention tang toward the fourth opening 29 in the inferior surface 12.

In some embodiments, the intervertebral implant 100, 200, 300, 400, 500 further comprises: a first fixation aperture 18 in the anterior wall; an insert plate 50 configured to be coupled to the spacer body 10, the insert plate comprising a second fixation aperture 51 extending therethrough configured to coaxially align with the first fixation aperture; wherein the first fixation aperture and second fixation aperture are configured to receive a locking mechanism 70.

In some embodiments, the intervertebral implant further comprises: a faceplate or spinal cage fixation plate 40 and the locking mechanism 70; wherein the faceplate comprises a third fixation aperture 47 extending therethrough and a counter-bore 48, both configured to coaxially align with the first fixation aperture 18 in the spacer body and the second fixation aperture 51 in the insert plate 50, wherein the locking mechanism 70 is configured to pass through the third fixation aperture and into the coaxially aligned second and first fixation apertures to securely retain the faceplate or spinal cage fixation plate against the anterior wall 13 of the spacer body, wherein a locking mechanism head or cap 71 is captured within the counter-bore 47, and wherein the faceplate or spinal cage fixation plate is further configured to be a secondary capture mechanism for the first bone fixation member(s) 30 to prevent unintentional removal thereof.

Provided herein is an intervertebral implant comprising: a bone fixation member also called a retainer 30 comprising: a cap 35 with an anterior 31 and posterior surface 32; a capture feature on the cap; a first retention tang and a second retention tang each retention tang having a first end, a lengthwise body and a second end opposite the first end and forming a split-fork configuration relative to each other; wherein the first retention tang and second retention tang protrude from the posterior face of the cap, each retention tang in a plane parallel to the other retention tang.

In some embodiments, the first end of each retention tang is affixed to and protruding from the posterior surface of the cap, wherein the second end of each retention tang is oriented at a non-perpendicular angle to the posterior surface of the cap and each second end is oriented in divergent directions to the other retention tang.

In some embodiments, each retention tang of the bone fixation member is configured such that the lengthwise body of each retention tang is straight, arcuate, or helical between the first end and the second end.

Provided herein is a spinal cage fixation plate comprising: an anterior surface; a stepped posterior surface spaced from the anterior surface along a medial-lateral direction; a superior surface; and an inferior surface spaced from the superior surface along a medial-lateral direction; a first fixation aperture extending from the anterior surface through the posterior surface, configured to receive the shank of a fixation mechanism; and a concentric secondary aperture on the anterior surface, coaxially aligned with the first fixation aperture, configured to receive the head of the fixation mechanism, wherein the first fixation aperture and secondary aperture are centrally located in the medial-lateral and superior-inferior dimensions of the fixation plate, wherein an overall medial-lateral dimension of the plate is greater than a superior-inferior dimension of the plate, and wherein the stepped posterior surface comprises a recessed medial stepped portion, a recessed lateral stepped portion and a posteriorly protruding central portion.

In some embodiments, the surfaces of the recessed medial stepped portion, and the recessed lateral stepped portion are defined as a coaxial cylindrical surface, the curvature approximating that of vertebral bodies to be fused, when viewed from a superior or inferior orientation.

In some embodiments, the posteriorly protruding central portion is configured to align with and interface with a mating recessed surface on an anterior face of a spinal fusion cage, and wherein the first fixation aperture and secondary aperture are configured to coaxially align with a mating third aperture in the anterior portion of said spinal fusion cage and jointly accept a fixation mechanism configured to secure the spinal cage fixation plate to the spinal fusion cage, and wherein the surfaces of the recessed medial stepped portion, and the recessed lateral stepped portion of the spinal cage fixation plate are configured to align with a raised anterior medial stepped portion, and a raised anterior lateral stepped portion of the fusion cage.

In some embodiments, the spinal cage fixation plate further comprises: at least one aperture for receiving a bone screw; wherein the at least one aperture is positioned superiorly to the superior surface of the fixation plate and configured to at least temporarily secure the fixation plate to a superior adjacent vertebra.

In some embodiments, the spinal cage fixation plate further comprises at least a second aperture for receiving a bone screw; wherein the at least second aperture is positioned inferiorly to the inferior surface of the fixation plate and configured to at least temporarily secure the fixation plate to an inferior adjacent vertebra.

In some embodiments, the spinal cage fixation plate further comprises at least one fixation spike; wherein the at least one fixation spike is positioned superiorly to the superior surface of the fixation plate and configured to at least temporarily secure the fixation plate to a superior adjacent vertebra.

In some embodiments, the spinal cage fixation plate further comprises at least a second fixation spike; wherein the at least second fixation spike is positioned inferiorly to the inferior surface of the fixation plate and configured to at least temporarily secure the fixation plate to an inferior adjacent vertebra.

In some embodiments, the spinal cage fixation plate further comprises: anteriorly recessed features in the posterior surfaces of the recessed medial stepped portion, and the recessed lateral stepped portion of the spinal cage fixation plate configured to align with and capture the cap of a bone fixation member protruding from the anterior face of a spinal fusion cage; and a capture ring or retaining clip configured to capture the cap of bone fixation member within the anteriorly recessed feature.

In some embodiments, the spinal cage fixation plate comprises at least one of: a biologically inert material; a sufficiently porous surface to facilitate bony ingrowth; and a biologically active surface coating to facilitate bony ingrowth and spinal fusion.

In some embodiments, the surfaces of the recessed medial stepped portion, and the recessed lateral stepped portion of the spinal cage fixation plate are configured to align with an anterior surface of a superior and inferior vertebra, wherein the posteriorly protruding central portion is configured to fit between and separate the inferior surface of the superior vertebra and superior surface of the inferior vertebra.

In some embodiments, the posteriorly protruding central portion is further configured to prevent the expulsion of a spinal fusion cage positioned between the inferior and superior vertebrae.

In some embodiments, the at least first fixation spike and the at least second fixation spike further comprise at least one: a biologically inert material; a sufficiently porous surface to facilitate bony ingrowth; and a biologically active coating to facilitate bony ingrowth.

In some embodiments, the fixation plate is made of a biologically inert material selected from the group consisting of: an allograft; an autograft; titanium; titanium alloys; PEEK (polyaryl, ether, ether ketone) polymer; cobalt-chromium alloys; tantalum; tantalum alloys; niobium; niobium alloys; and stainless steel.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An intervertebral implant for positioning between a first vertebra and a second vertebra successive to the first vertebra, the intervertebral implant comprising:
   a spacer body comprising;
      a superior surface configured to contact an inferior endplate of the first vertebra,
      an inferior surface configured to contact a superior endplate of the second vertebra,
      an anterior wall,
      a posterior wall,
      a first lateral wall extending between the posterior wall and the anterior wall,
      a second lateral wall extending between the posterior wall and the anterior wall, and
      an interior graft window defined by the anterior wall, the posterior wall, the first lateral wall and the second lateral wall, the interior graft window comprising;
      a graft aperture open to either the superior surface, the inferior surface or both the superior surface and the inferior surface;
   a first bone fixation member;
   a second bone fixation member;
   a first ramped channel extending from the anterior wall to the superior surface within the first lateral wall and configured to guide the first bone fixation member into the first vertebra; and
   a second ramped channel extending from the anterior wall to the inferior surface within the same first lateral wall and configured to guide the second bone fixation member into the second vertebra; and
   a first locking mechanism comprising one or more capture tangs transversely slidable along a direction relative to the first bone fixation member and the second bone fixation member to lock the first bone fixation member and the second bone fixation member relative to the anterior wall.

2. The intervertebral implant of claim 1, wherein at least one of the first bone fixation member and the second bone fixation member comprises:
   a cap with an anterior and posterior surface;
   a capture feature on the cap;
   a first retention tang and a second retention tang forming a split-fork configuration;
   wherein the first retention tang and second retention tang protrude from the posterior surface of the cap.

3. The intervertebral implant of claim 2, further comprising a first split-guide, wherein the first bone fixation member is configured to be inserted through the first split-guide wherein the first ramped channel is configured to guide the first retention tang toward a first opening in the anterior wall and the second ramped channel is configured to guide the second retention tang toward a second opening in the inferior surface.

4. The intervertebral implant of claim 3, further comprising:
   a second split-guide in the anterior wall, the second split-guide comprising:
      a third ramped channel extending from the anterior wall to the superior surface within the second lateral wall; and
      a fourth ramped channel extending from the anterior wall to the inferior surface within the same second lateral wall.

5. The intervertebral implant of claim 2, wherein each retention tang of a bone fixation member has a first end, a lengthwise body, and a second end opposite the first end,
   wherein the split-fork configuration is relative to the posterior surface of the cap,
   wherein the first end of a retention tang is affixed to and protrudes from the posterior surface of the cap, being in a plane parallel to the first end of another retention tang, and
   wherein the second end of a retention tang is oriented at a non-perpendicular angle relative to the posterior surface of the cap, being oriented in a divergent direction relative to a direction of the second end of another retention tang.

6. The intervertebral implant of claim 5, wherein at least one of the two retention tangs further comprises a plurality of substantially inversely shaped "V" notches along the lengthwise body, anywhere between a middle of the lengthwise body and proximate to the second end, the plurality of notches configured to promote resistance to extraction of the at least one of the two retention tangs and the overall bone fixation member from a vertebral bone or the spacer body after insertion.

7. The intervertebral implant of claim 2, further comprising a first split-guide and retaining clip configured to capture the bone fixation member within the opening of the first split-guide or a second split-guide.

8. The intervertebral implant of claim 1, further comprising:
   a first fixation aperture in the anterior wall extending to the interior graft window;
   an insert plate configured to be coupled to the spacer body within the interior graft window, the insert plate comprising a second fixation aperture extending therethrough configured to coaxially align with the first fixation aperture;
   wherein the first fixation aperture and second fixation aperture are configured to receive a second locking mechanism.

9. The intervertebral implant of claim 8, further comprising:
   a faceplate or spinal cage fixation plate,
   wherein the faceplate or spinal cage fixation plate comprises an anterior face, a stepped posterior face, top edge, a bottom edge spaced apart from the top edge, a first lateral edge, and a second lateral edge,
   wherein the faceplate or spinal cage fixation plate further comprises a third fixation aperture extending therethrough and a counter-bore, both the third fixation aperture and the counter-bore configured to coaxially align with the first and second fixation apertures,
   wherein the second locking mechanism is configured to pass through the third fixation aperture and into the first and second fixation apertures to securely retain the faceplate or spinal cage fixation plate against the anterior wall of the spacer body,
   wherein a locking mechanism head or cap is captured within the counter-bore;
   wherein the faceplate or spinal cage fixation plate is further configured to be a capture mechanism for at least the first bone fixation member to prevent unintentional removal thereof; and wherein the second locking mechanism comprises:
a screw;
a bolt;
a bayonette connection;
a pin; or
a split-compression pin.

10. The intervertebral implant of claim 1, further comprising a first-split guide, wherein the first split-guide is configured to receive the first bone fixation member comprising a cap with two retention tangs and provide a guided pathway to simultaneously direct the two retention tangs in opposite directions such that when the bone fixation member is impacted, the first of two tangs at least partially penetrates the inferior endplate of the first vertebra and the second of two tangs simultaneously, at least partially penetrates the superior endplate of the second vertebra.

11. The intervertebral implant of claim 1, further comprising a first split-guide, comprising:
a first of two ramped channels having a first end at a first split-guide aperture, a lengthwise pathway, and a second end providing an opening to the superior surface within a lateral wall; and
a second of two ramped channels having a first end at a second split-guide aperture, a lengthwise pathway, and a second end providing an opening to the inferior surface within the same lateral wall;
wherein each ramped channel lengthwise pathway is shaped such that the configuration of the lengthwise pathway is:
straight;
arcuate; or
helical;
between the first end and the second end of each respective ramped channel.

12. An intervertebral implant comprising:
a spacer body;
a first locking mechanism; and
a bone fixation member comprising:
a cap with an anterior surface and a posterior surface;
a capture feature on the cap;
a first retention tang;
wherein the first retention tang protrudes from the posterior surface of the cap;
wherein the first locking mechanism is configured to contact the capture feature to retain the bone fixation member relative to the spacer body; and
wherein the capture feature is on a peripheral surface, of the cap, the peripheral surface oriented perpendicular to the posterior surface.

13. The intervertebral implant of claim 12, wherein a first end of each retention tang is affixed to and protruding from the posterior surface of the cap, and
wherein a second end of each retention tang is oriented at a non-perpendicular angle to the posterior surface of the cap and each second end is oriented in divergent directions to the other retention tang.

14. The intervertebral implant of claim 13, wherein each retention tang of the bone fixation member is configured such that a lengthwise body of each retention tang is:
straight;
arcuate; or
helical;
between a first end and a second end.

15. The intervertebral implant of claim 12, further comprising a second locking mechanism, operable independently of the first locking mechanism, configured to lock the bone fixation member relative to the spacer body.

16. The intervertebral implant of claim 15, wherein the second locking mechanism comprises a head-driven screw configured to lock a spinal cage fixation plate in a location anterior to the bone fixation member.

17. The intervertebral implant of claim 15, further comprising one or more additional bone fixation members having one or more additional capture features, wherein the second locking mechanism comprises one or more capture tangs configured to retain the one or more additional bone fixation members relative to the spacer body using the one or more additional capture features.

18. The intervertebral implant of claim 12, wherein the first locking mechanism comprises a capture tang transversely slidable along a direction relative to the bone fixation member to engage the capture feature to lock the bone fixation member relative to an anterior wall of the spacer body.

19. The intervertebral implant of claim 12, wherein the first locking mechanism comprises a retaining clip transversely slidable along a direction relative to the bone fixation member to engage the capture feature to lock the bone fixation member relative to an anterior wall of the spacer body.

20. An intervertebral implant for positioning between a first vertebra and a second vertebra successive to the first vertebra, the intervertebral implant comprising:
a spacer body comprising;
a superior surface configured to contact an inferior endplate of the first vertebra,
an inferior surface configured to contact a superior endplate of the second vertebra,
an anterior wall,
a posterior wall,
a first lateral wall extending between the posterior wall and the anterior wall,
a second lateral wall extending between the posterior wall and the anterior wall, and
an interior graft window defined by the anterior wall, the posterior wall, the first lateral wall and the second lateral wall, the interior graft window comprising;
a graft aperture open to either the superior surface, the inferior surface or both the superior surface and the inferior surface;
a first bone fixation member;
a second bone fixation member;
a first ramped channel extending from the anterior wall to the superior surface within the first lateral wall and configured to guide the first bone fixation member into the first vertebra; and
a second ramped channel extending from the anterior wall to the inferior surface within the same first lateral wall and configured to guide the second bone fixation member into the second vertebra;
a first locking mechanism configured to lock the first bone fixation member and the second bone fixation member relative to the anterior wall; and
a second locking mechanism, operable independently of the first locking mechanism, configured to lock the first bone fixation member and the second bone fixation member relative to the anterior wall.

21. An intervertebral implant comprising:
a plurality of bone fixation members;
a spacer body comprising an anterior surface comprising:
a plurality of bone fixation holes positioned to receive the bone fixation members; and
a fixation aperture that is centered on the anterior surface; and a spinal cage fixation plate attachable to the spacer body, the spinal cage fixation plate comprising:
  an anterior surface;
  a posterior surface;
  a superior surface;
  and an inferior surface spaced from the superior surface along a cephalad-caudal direction;
  a first fixation aperture extending from the anterior surface through the posterior surface, configured to receive a shank of a fixation mechanism received in the fixation aperture of the spacer body; and
  wherein a medial-lateral width of the spinal cage fixation plate is at least as large as a medial-lateral width of the spacer body such that, with the spinal cage fixation plate secured to the spacer body, the spinal cage fixation plate covers the bone fixation holes.

* * * * *